United States Patent
Chen et al.

(10) Patent No.: US 9,771,607 B2
(45) Date of Patent: Sep. 26, 2017

(54) **METHOD OF CONSTRUCTING A RECOMBINANT *BACILLUS SUBTILIS* THAT CAN PRODUCE SPECIFIC-MOLECULAR-WEIGHT HYALURONIC ACIDS**

(71) Applicants: Jian Chen, Wuxi (CN); Zhen Kang, Wuxi (CN); Guocheng Du, Wuxi (CN); Peng Jin, Wuxi (CN)

(72) Inventors: Jian Chen, Wuxi (CN); Zhen Kang, Wuxi (CN); Guocheng Du, Wuxi (CN); Peng Jin, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 69 days.

(21) Appl. No.: 15/011,509

(22) Filed: Jan. 30, 2016

(65) Prior Publication Data
US 2017/0073719 A1  Mar. 16, 2017

(30) Foreign Application Priority Data

Sep. 10, 2015  (CN) .......................... 2015 1 0573851

(51) Int. Cl.
| | | |
|---|---|---|
| *C07K 14/00* | (2006.01) | |
| *C12P 19/26* | (2006.01) | |
| *C12N 9/26* | (2006.01) | |
| *C12N 9/04* | (2006.01) | |
| *C12N 9/12* | (2006.01) | |
| *C12N 9/90* | (2006.01) | |
| *C12N 9/10* | (2006.01) | |

(52) U.S. Cl.
CPC ............ *C12P 19/26* (2013.01); *C12N 9/0006* (2013.01); *C12N 9/1096* (2013.01); *C12N 9/1241* (2013.01); *C12N 9/2474* (2013.01); *C12N 9/90* (2013.01); *C12Y 101/01022* (2013.01); *C12Y 206/01016* (2013.01); *C12Y 207/07009* (2013.01); *C12Y 207/07023* (2013.01); *C12Y 302/01035* (2013.01); *C12Y 504/0201* (2013.01)

(58) Field of Classification Search
CPC .... C12Y 302/01035; C12Y 302/01036; C12Y 402/02001
See application file for complete search history.

(56) References Cited

PUBLICATIONS

Widner et al. 2005; Hyaluronic acid production in Bacillus subtilis. Applied and Environmental Microbiology. 71(7): 3747-3752.*
Jin et al. 2014; High yield novel leech hyaluronidase to expedite the preparation of specific hyaluronan oligomers. Scientific Reports. 4(4471):1-8.*

* cited by examiner

*Primary Examiner* — Karen Cochrane Carlson
(74) *Attorney, Agent, or Firm* — Lili Chen

(57) ABSTRACT

The present invention relates to the field of biotechnology engineering. It provides a method of constructing a recombinant *Bacillus subtilis* that can produce specific-molecular-weight hyaluronic acids. By integranted expression of hasA from *Streptococcus zooepidemicus* and overexpression of genes of HA synthetic pathway, tuaD, glmU and glmS, high yield HA production was achieved in the recombinant strain. Additionally, introduction and functional expression of the leech hyaluronidase in the recombinant strain substantially increased the yield of HA to 19.38 $g \cdot L^{-1}$. Moreover, HAs with a broad range of molecular weights ($10^3$ Da to $10^6$ MDa) were efficiently produced by controlling the expression level of hyaluronidase using RBS mutants with different translational strengths. The method of the present invention can be used to produce low molecular weight HAs at large scale in industrial applications.

10 Claims, 6 Drawing Sheets

METHOD OF CONSTRUCTING A RECOMBINANT *BACILLUS SUBTILIS* THAT CAN PRODUCE SPECIFIC-MOLECULAR-WEIGHT HYALURONIC ACIDS

CROSS-REFERENCES AND RELATED APPLICATIONS

This application claims the benefit of priority to Chinese Application No. 201510573851.X, entitled "A method of constructing a recombinant *Bacillus subtilis* that can produce specific-molecular-weight hyaluronic acids", filed Sep. 10, 2015, which is herein incorporated by reference in its entirety.

BACKGROUND OF THE INVENTION

Field of the Invention

The present invention relates to the field of biotechnology engineering, and more particularly relates to a method of constructing a recombinant *Bacillus subtilis* that can produce specific-molecular-weight hyaluronic acids.

Description of the Related Art

Hyaluronic Acid (HA or hyaluronan), a highly viscous polysaccharide, was first isolated from bovine vitreous and it is the best moisturizing substances found in nature. The unique rheological, the viscoelastic and hygroscopic properties along with the biocompatibility and non-immunogenicity has enabled HA to be widely used in cosmetics, food and pharmaceutics. Recent studies have found that HAs with low molecular weight (less than $1 \times 10^4$ Da) and HA oligosaccharides have unique biological functions, for example, HA oligosaccharides with molecular weight less than $1 \times 10^4$ Da are involved in wound healing and tumor cell apoptosis. In addition, the HA oligosaccharides can be easily absorbed by human body and act as precursors for the body's own synthesis of polysaccharides. Therefore, HA oligosaccharides have important applications in the areas of food, health care and medicine.

HA is widely distributed in animal tissues, such as comb, synovial fluid, cartilage and vitreous. And it is also distributed in bacteria, such as *Bacillus aerogenes, Pseudomonas aeruginosa* and *Hemolytic streptococcus*. Due to disadvantages (such as the risk of cross-species viral infection) of the traditional HA extraction methods from animal tissues, the commercial HA production is mainly relied on fermentation of certain attenuated strains of group C *Streptococcus* (such as *S. equi* and *S. zooepidemicus*). The HA produced by microbial fermentation was mostly high molecular weight HA. With increasing health and safety requirements, it becomes more and more urgent to find a safe and reliable microbial host for HA production.

Although de novo synthesis methods for preparing HA oligosaccharides have been reported, it is difficult to achieve large-scale production due to high cost of substrates, complex synthesis steps and low yields. Currently, physical and chemical degradation are the main methods used for low-molecular weight HA production, which have many disadvantages, such as generation of HA with a wide range of molecular weight distribution, poor product stability, high cost of purification, high energy consumption and high pollution. Compared to physical or chemical degradation, enzymatic catalytic synthesis of HA oligosaccharides is a promising approach that offers great industrial potential. However, the enzymatic method requires preparation of large amount of hyaluronidase (HAase) and precise control of the enzymatic catalytic reaction conditions. Therefore, constructing a single microbial strain that simultaneously produces both HA and HAase can offer great benefits in HA research and industrial applications.

HAase is a class of hyaluronic acid-degrading enzymes widely distributed in nature. According to sources, structures and function mechanisms of the enzyme, HAase are divided into three categories: endo-β-N-acetyl-glucosaminidase (EC 3.2.1.35, mainly exist in mammals and venom of bees, snakes and spiders), endo-β-glucuronidase enzyme (EC 3.2.1.36, mainly in the leech) and hyaluronic acid lyase (EC 4.2.2.1, mainly exist in bacteria, bacteriophages and fungi). As a "scatter factor", HAase is widely used as auxiliaries for drug diffusion in clinical applications. However, the commercial HAase obtained from bovine testicular tissue is usually of poor quality and expensive to produce, and has the risk of Animal foci infection.

In the present invention, a HA biosynthetic pathway was constructed in *Bacillus subtilis* (*B. subtilis*) and high yield of HA was achieved by regulating the expression of important genes for synthesis of HA precursors, UDP-GlcNAc and UDP-GlcA, in the engineered strain. In addition, Leech HAase was co-expressed in the engineered strain with a HA biosynthetic pathway to achieve synchronous production of HA and HAase. Production of HA with specific molecular weights was achieved by precise regulation of the expression levels of HAase. The problem of fermentation stagnation caused by high viscosity of HA was solved by coupling the production of HA and HAase, thus greatly increasing the production efficiency. The present invention for the first time achieved efficient synthesis of HA with specific molecular weights, which has potential for bringing great economic gains in industrial applications.

DETAILED DESCRIPTION

The present invention provides a recombinant *B. subtilis* that can produce HA having molecular weights within specific ranges (specific-molecular-weight HA). A HA synthetic pathway is constructed and a HAase is coexpressed in the recombinant strain; and the RBS (ribosome binding sites) optimization strategy is performed to regulate the expression levels of HAase at the translational level, which in turn regulates the average molecular weight of HA products.

In one embodiment, the present invention provides a recombinant *B. subtilis* that the molecular weight of HA products in the recombinant strain is controlled by the expression level of HAase, wherein the higher is the expression of HAase, the lower is the molecular weight of the HA product and the higher is the yield of HA production.

In one embodiment of the present invention, a regulatory DNA fragment and a HAase gene are integrated into the genome of a *B. subtilis* containing a HA synthetic pathway. The said regulatory DNA fragment contains a constitutive promoter $P_{lepA}$, a RBS sequence and a signal peptide. In one embodiment, the nucleotide sequences of the regulatory DNA fragment is set forth in SEQ ID NO: 8, SEQ ID NO: 12 or SEQ ID NO: 13. The DNA integration in the recombinant strain is mediated by plasmid pBlueScript SK (+).

In one embodiment of the present invention, the *B. subtilis* host is *B. subtilis* 168.

In one embodiment of the present invention, the nucleotide sequence of the HAase is SEQ ID NO: 7.

In one embodiment of the present invention, genes of the HA synthetic pathway contains hasA, which encodes a hyaluronan synthase. The hasA is derived from *Streptococcus zooepidemicus*, *Streptococcus equi* or *Streptococcus equissp*.

In one embodiment of the present invention, the hasA is derived from *Streptococcus zooepidemicus* with a nucleotide sequence of SEQ ID NO: 1.

In one embodiment of the present invention, the HA biosynthetic pathway is obtained by further constructing a biosynthetic pathway for HA precursors, UPD-N-acetylglucosamine (UDP-GlcNAc) and UDP-D-glucuronide (UDP-GlcA), in a recombinant *B. subtilis* containing a hyaluronan synthase.

In one embodiment of the present invention, genes of UDP-GlcA and UDP-GlcNAc biosynthetic pathway are derived from *Streptococcus* species, *Escherichia coli* or *Bacillus*. In one embodiment of the present invention, the genes are derived from *B. subtilis*, containing tuaD (the nucleotide sequence is SEQ ID NO: 2) which encodes a UDP-glucose dehydrogenase, glmU (the nucleotide sequence is SEQ ID NO: 3) which encodes a UDP-N-acetylglucosamine pyrophosphorylase, gtaB (the nucleotide sequence is SEQ ID NO: 4) which encodes a UDP-glucose pyrophosphorylase, glmM (the nucleotide sequence is SEQ ID NO: 5) which encodes a mutase and glmS (the nucleotide sequence is SEQ ID NO: 6) which encodes an amino transferase.

In one embodiment of the present invention, the HAase gene deriving from leeches is fused with a signal peptide and a promoter, and then integrated into a recombinant *B. subtilis* with a HA biosynthetic pathway.

The present invention provides a method of constructing a recombinant *B. subtilis* that produces specific-molecular-weight HA. The method comprises the following steps:

(1) construction of a HA biosynthetic pathway: a hyaluronan synthase hasA gene is inserted into plasmid pAX01, and the obtained recombinant plasmid is transformed into *B. subtilis*, resulting in the hasA gene integrated into the genome of *B. subtilis* under the control of Pxyl promoter. The recombinant *B. subtilis* strain is designated as E168T. The tuaD and glmU are respectively fused with strong ribosome binding site, P43. The gtaB was fused with promoter Pveg and P43 RBS, the glmM and glmS were respectively fused with P43 RBS. The five fused fragments are connected in series and inserted into pP43NMK vector. The resulting recombinant plasmid is transformed into E168T. A recombinant *B. subtilis* with a HA biosynthetic pathway is thus obtained.

(2) The hyaluronidase gene is fused with PlepA promoter, a RBS and a signal peptide, and integrated into the genome of the recombinant *B. subtilis* obtained in step (1), resulting in a recombinant *B. subtilis* containing a HA biosynthetic pathway and HAase coexpression.

(3) Expression levels of the HAase in step (2) are precisely controlled by the translational strength of different RBS sequences, the higher the translational strength of the RBS, the lower the molecular weight of HA produced by the recombinant *B. subtilis*.

In one embodiment of the present invention, hasA gene is integrated at the lacA (β-galactosidase gene) locus of *B. subtilis* chromosome in the step (1).

In one embodiment of the present invention, hyaluronidase gene is integrated at the glucosamine-6-phosphate deaminase 1 (nagA-nagBA) locus of *B. subtilis* chromosome in the step (2).

In one embodiment of the present invention, the expression of HAase in step (2) is controlled by the wild-type RBS with a nucleotide sequence of aggaggaa (contained in the regulatory DNA fragment shown in SEQ ID NO:8). The average molecular weight of HA produced by the recombinant is 6628 dalton, the HAase activity reaches $1.62 \times 10^6$ U/mL and the yield of HA reaches 19.38 g/L.

In another embodiment of the present invention, the expression of HAase in step (2) is controlled by RBS mutant R1 with a nucleotide sequence of aagaggag (contained in the regulatory DNA fragment shown in SEQ ID NO:12). The average molecular weight of HA produced by the recombinant is 18,000 dalton, the HAase activity reaches $8.8 \times 10^5$ U/mL and the yield of HA reaches 9.18 g/L.

In another embodiment of the present invention, the expression of HAase in step (2) is controlled by RBS mutant R2 with a nucleotide sequence of acgtagac (contained in the regulatory DNA fragment shown in SEQ ID NO:13). The average molecular weight of HA produced by the recombinant is 49,600 dalton, the HAase activity reaches $6.4 \times 10^4$ U/mL and the yield of HA reaches 7.13 g/L.

In another embodiment of the present invention, the average molecular weight of HA produced by the recombinant strain obtained in step (1), which has no expression of HAse, is 1,420,000 dalton and the yield of HA is 5.96 g/L.

The present invention also provides a method of producing specific-molecular-weight HA ($10^3$ Da<Mr<$10^6$ Da) by using the recombinant *B. subtilis* strain. The method is performed by cultivating the recombinant in a 3 L fermenter with a fed-batch fermentation strategy at 37° C. for 56-96 hours, and specific-molecular-weight HA ranging from 6628 Da to 1420000 Da can be obtained. The medium for cultivation contains 5% yeast extract, 2% sucrose, 15.6 g/L sodium dihydrogen phosphate and 3.9 g/L potassium sulfate. In addition, the main products are low-molecular-weight HA (LMW-HA) or HA oligosaccharides (HA-4, HA-6, HA-8, HA-10, and so on) if secreted HAase is allowed to continue digesting the HA product after the end of fermentation.

In one embodiment, the carbon source in the cultivation medium is sucrose.

In one embodiment, the fermentation temperature is 37° C.

In one embodiment of the present invention, the fermentation time is set differently according to different recombinant strains.

After separation and purification, the HAase in the fermentation broth can be used in food, medical or clinical applications.

Compared with other engineered strains, the HA producing recombinant of the present invention has many advantages. Firstly, the present invention uses the food grade host of the recombinant strain that meets the requirements of health and food safety, and does not have any infection risk of endotoxins or pathogens. Secondly, the high molecular weight HA produced by the recombinant strain is degraded into LMW-HA by an extracellularly secreted HAase. The biosynthesis of HA is coupled with secretory expression of HAase in the present invention to reduce the viscosity of the fermentation broth, thus increasing the dissolved oxygen and enhance the yield of HA. Additionally, the molecular weight of HA in fermentation broth could be precisely controlled with a broad range from $10^3$ to $10^6$ Da, and purification and recovery of final products is very simple and easy to operate. Therefore, the method of the present invention has great value for large-scale production of specific low-molecular-weight hyaluronic acids.

EXAMPLES

Figure 1:
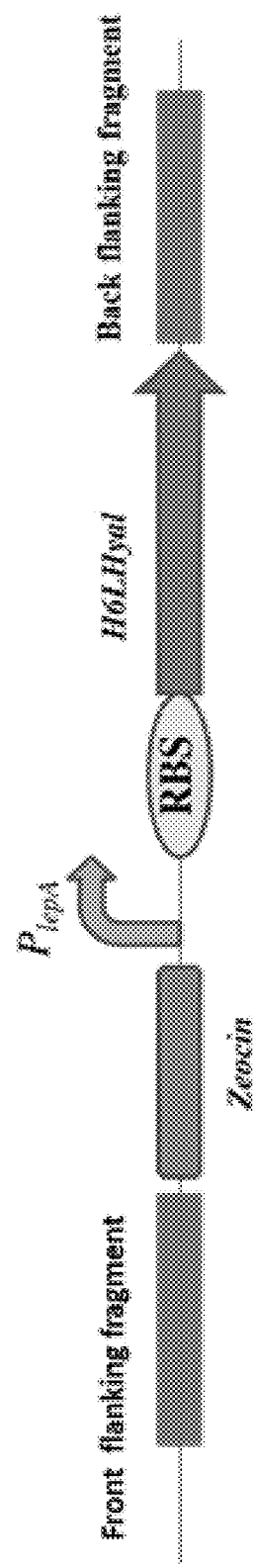
FIG. 1. Construction schematic of the regulatory DNA fragment for controlling HAase expression.

Materials and Methods:
Information of related nucleotide sequences:
(1) SEQ ID NO: 1 is the nucleotide sequence of hyaluronic acid synthase gene hasA from *Streptococcus pneumoniae*.
(2) SEQ ID NO: 2 is the nucleotide sequence of UDP-glucose dehydrogenase gene tuaD from *B. subtilis*.
(3) SEQ ID NO: 3 is the nucleotide sequence of UDP-N-acetylglucosamine pyrophosphorylase gene glmU from *B. subtilis*.
(4) SEQ ID NO: 4 is the nucleotide sequence of UDP-glucose pyrophosphorylase gene gtaB from *B. subtilis*.
(5) SEQ ID NO: 5 is the nucleotide sequence of a mutase gene glmM from *B. subtilis*.
(6) SEQ ID NO: 6 is the nucleotide sequence of an amino transferase gene glmS from *B. subtilis*.
(7) SEQ ID NO: 7 is the nucleotide sequence of a Leech hyaluronidase gene.
(8) SEQ ID NO: 8 is the nucleotide sequence of a regulatory DNA fragment $P_{lepA}$-RBS-yewA.
(9) SEQ ID NO: 9 is the nucleotide sequence of a bleomycin resistant gene.
(10) SEQ ID NO: 10 is the nucleotide sequence of constitutive promoter P43.
(11) SEQ ID NO: 11 is the nucleotide sequence of inducible promoter Pveg.
(12) SEQ ID NO: 12 is the nucleotide sequence of a regulatory DNA fragment $P_{lepA}$-RBS1-yewA.
(13) SEQ ID NO:13 is the nucleotide sequence of a regulatory DNA fragment $P_{lepA}$-RBS2-yewA.

The HA titers were routinely estimated by the modified carbazole assay. The HA titer is assumed to be 2.067 times the glucuronic acid titer.

Leech hyaluronidase (LHAse or LHyal) activity was quantified by measuring the amount of reducing sugar liberated from HA using the 3,5-dinitrosalicylic acid (DNS) colorimetric spectrophotometric method. One unit of enzymatic activity is defined as equal to the reducing power of glucuronic acid (glucose equivalents in micrograms) liberated per hour from HA at 38° C., pH 5.5. Specific activity is defined as units of enzyme per ml of culture supernatant. The standard enzymatic reaction contained appropriate volumes of fermentation supernatant and 1.6 mg·ml$^{-1}$ of HA as the substrate was incubated in 50 mM citrate-disodium hydrogen phosphate buffer at 38° C., pH 5.5 for 10 min in a total volume of 1 ml. The reaction was stopped by immersing in boiling water for 2 min and the enzyme activity was examined using the DNS method. Controls with fermentation supernatant of *B. subtilis* 168 were prepared and analyzed in the same manner The average molecular weight of HA was measured by high performance gel filtration chromatography (HPGFC) with a multi-angle laser light scattering detector (MALLS). The mobile phase was 0.1 mol·L$^{-1}$ NaNO$_3$ and the temperature of the column was maintained at 40° C. The sample size was 40 μL and elution time for each sample was 25 min. Dextran produced from Chinese Institute of food and drug testing was used as a standard and GPC software was used to calculate the average molecular weight.

Example 1

Construction of the Recombinant Plasmid pAX01-hasA

Hyaluronan synthase hasA was cloned from *S. zooepidemicus* ATCC 35246 with primers hasA-F/hasA-R to amplify the hasA gene by polymerase chain reaction (PCR). The *S. zooepidemicus* strain was incubated in 5 mL M17 media at 37° C., 200 rpm for 16 hours, and the chromosome of *S. zooepidemicus* was extracted by a bacterial genome extraction kit.

The nucleotide sequences of primers hasA-F and hasA-R were as follows (from 5' to 3'):

```
hasA-F:
                                    (SEQ ID NO: 15)
CGCGGATCCATGAGAACATTAAAAAACCTCATAAC hasA-R:
                                    (SEQ ID NO: 16)
TGCATGCATTTATAATAATTTTTTACGTGTTCC
```

Gene fragment of hasA amplified by PCR and pAX01 plasmid were digested with restriction enzymes BamHI and SacII, respectively. The digested fragments were recovered for ligation. Then the ligation products were used to transform to JM109 competent cells and positive recombinant plasmid pAX01-hasA was verified by sequencing. Then, the pAX01-hasA was transformed into *B. subtilis* 168, resulting in the hasA gene integrated into the genome of *B. subtilis* 168 under the control of Pxyl promoter. The recombinant strain was designated as E168T.

Example 2

Construction of the Recombinant Plasmid pP43NMK/pP43-DU-PBMS tuaD gene and glmU gene were amplified from *B. subtilis* 168 by PCR using primers tuaD-F/tuaD-R and glmU-F/glmU-R, respectively. KpnI restriction site and P43 RBS sequence (shown in SEQ ID NO:14) were introduced to the 5' of tuaD-F. SacI restriction site was introduced to the 5' of tuaD-R. SacI restriction site and P43 RBS sequence were introduced to the 5' of glmU-F. XhoI and XbaI restriction sites were introduced to the 5' of glmU-R. The resulting tuaD fragment and glmU fragment were digested with KpnI/SacI and SacI/XhoI, respectively. The digested fragments were purified and ligated together with digested pP43NMK (KpnI/XhoI) fragment. Then, the obtained ligation product was transformed into JM109 competent cells. The positive recombinant cells was verified by sequencing and the recombinant plasmid was designated as pP43-DU.

The Pveg promoter fragment amplified with the primer pair Pveg-F/Pveg-R was fused with the gtaB gene amplified with the primer pair Pveg-gtaB-F(containing a P43 RBS) and gtaB-R. SpeI and XbaI-XhoI restriction sites were introduced to the 5' and the 3' of the fusion fragment, respectively. The fusion product was digested with SpeI and XhoI, and ligated with digested pP43-DU fragment (XbaI and XhoI), resulting in a recombinant plasmid designated as pP43-DU-PB.

By use of the same isocaudarner SpeI/XbaI, glmM and glmS genes were amplified with primers glmM-F/R and glmS-F/R, respectively. The glmM and glmS fragments were inserted into plasmid pP43-DU-PB in order, generating the recombinant plasmid pP43-DU-PBMS. pP43-DU-PBMS was transformed into E168T competent cells and a recombinant strain E168T/pP43-DU-PBMS with high yield of HA was obtained.

The primers used were as follows:

```
tuaD-F:
                                        (SEQ ID NO: 17)
CGGGGTACCAAGAGAGGAATGTACACATGAAAAAAATAGCTGTCATTGG tuaD-R:
                                        (SEQ ID NO: 18)
CCGGAGCTCTTATAAATTGACGCTTCCCAAG glmU-F:
                                        (SEQ ID NO: 19)
CGGGAGCTCAAGAGAGGAATGTACACATGGATAAGCGGTTTGCAGTTG glmU-R:
                                        (SEQ ID NO: 20)
CCGCTCGAGCGGACTCTAGTCTAGATTATTTTTTATGAATATTTTTCAC Pveg-F:
                                        (SEQ ID NO: 21)
GGACTAGTGGAGTTCTGAGAATTGGTATGC Pveg-R:
                                        (SEQ ID NO: 22)
ATGTAAATCGCTCCTTTTTAACTAC Pveg-gtaB-F:
                                        (SEQ ID NO: 23)
GTAGTTAAAAGGAGCGATTTACATATGAAAAAAGTACGTAAAGC glmM-F:
                                        (SEQ ID NO: 24)
GGACTAGTAAGAGAGGAATGTACACATGGGCAAGTATTTTGGAACAG
ACGG glmM-R:
                                        (SEQ ID NO: 25)
CCGCTCGAGCGGACTCTAGTCTAGATTACTCTAATCCCATTTCTGAC
CGGAC glmS-F:
                                        (SEQ ID NO: 26)
GGACTAGTAAGAGAGGAATGTACACATGTGTGGAATCGTAGGTTATA
TCGG glmS-R:
                                        (SEQ ID NO: 27)
CCGCTCGAGCGGACTCTAGTCTAGATTACTCCACAGTAACACTCTTCGC
```

Example 3

Construction of the Integrated Gene Fragment of LHyal

The gene encoding hyaluronidase was integrated at the glucosamine-6-phosphate deaminase 1 (nagA-nagBA) locus of *B. subtilis* 168 using Zeocin gene as the selection marker. The integrated fragment (shown in FIG. 1) was obtained by homologous recombination technique.

The primers used were as follows:

```
H6LHyal-F:
                                        (SEQ ID NO: 28)
ATGCACAGTCTGCAGAATTCCACCACCACCACCACATG H6LHyal-R:
                                        (SEQ ID NO: 29)
TTACTTTTTGCACGCTTCAACAT ZHLHPlepA-F:
                                        (SEQ ID NO: 30)
CGCAGCCAAAGGAGTGGATTGCCTCAATCCTAGGAGAAACAG ZHLHPlepA-R:
                                        (SEQ ID NO: 31)
GAATTCTGCAGACTGTGCATGAGC ZHLH-front-F:
                                        (SEQ ID NO: 32)
TCAGCTGGTCTAGATCACTAGTC ZHLH-front-R:
                                        (SEQ ID NO: 33)
AATCCACTCCTTTGGCTGCGCTC ZHLH-zeocin-F:
                                        (SEQ ID NO: 34)
TTGAAGCGTGCAAAAAGTAAGAGCTCGGTACCCGGGGATCC ZHLH-zeocin-R:
                                        (SEQ ID NO: 35)
GCTTGCATGCCTGCAGGTCGAC ZHLH-back-F:
                                        (SEQ ID NO: 36)
CGACCTGCAGGCATGCAAGCCACTTCTTTCAGACGGAACCCTTGC ZHLH-back-R:
                                        (SEQ ID NO: 37)
CGGTCGTTCATATAGAAGTGATAG ZHLH-pSK-F:
                                        (SEQ ID NO: 38)
CACTTCTATATGAACGACCGCCTGTGTGAAATTGTTATCCGCTC ZHLH-pSK-R:
                                        (SEQ ID NO: 39)
TAGTGATCTAGACCAGCTGAGTGACTGGGAAAACCCTGGCGTTAC
```

The LHyal gene encoding a leech hyaluronidase (LHyal) was amplified with primers H6LHyal-F/H6LHyal-R and the Zeocin gene was amplified with primers ZHLH-zeocin-F/ZHLH-zeocin-R. The regulatory DNA fragment containing the promoter PlepA, the RBS P43 and the signal peptide yweA was amplified with primers ZHLHPlepA-F/R. The front and back flanking fragments of the target for integration were amplified with primers ZHLH-front-F/R and ZHLH-back-F/R, respectively. A recombinant vector was amplified with primers ZHLH-pSK-F/ZHLH-pSK-R using the plasmid pBlueScript SK(+) as template. The five DNA fragments and the recombinant vector described above were assembled using homologous recombination technology, and the assembled products were transformed into *E. coli* JM109 competent cells. The recombinant plasmid containing the regulatory DNA fragment and leech hyaluronidase gene was designated as pSKZHLH.

pSKZHLH was transformed into the competent cells of HA producing strain E168T/pP43-DU-PBMS and the recombinant strain was screened with 25 ug/ml Zeocin. The positive recombinant strain expressing HAase was designated as E168TH/pP43-DU-PBMS.

Example 4

Construction of RBS Mutant Library for Controlling the Expression of HAase

A RBS mutant library with a wide range of translational strength was constructed by genetic engineering at the ribosome regulation level. The degenerate primer JB/lepA-RBS-R, which includes the RBS region, and reverse primer ZHLH-H6F were used to amplify the RBS mutant library using the pSKZHLH as the template. KpnI restriction site was added to the 5' of both primers. The primers used were as follows:

```
JB/lepA-RBS-R:
                               (SEQ ID NO: 40)
ACGGGGTACCACTNTNYNHBYACTATTAAACGCAAAATACACTAGCTTAG ZHLH-H6F:
                               (SEQ ID NO: 41)
ACGGGGTACCATGCTAAAAAGAACTTCATTCG
```

The PCR product was first digested with DpnI, and then further digested with the restriction endonuclease KpnI, which was used for ligation. The ligation products were transformed into E168T/pP43-DU-PBMS competent cells. Five hundred transformants were picked from LB agar plates with 25 ug/ml Zeocin and then grown in 96-well microtiter at 37° C., 200 rpm for 60 hours. The culture medium contains 2% yeast powder, 7% sucrose, 15.6 g/L sodium dihydrogen phosphate, 3.9 g/L potassium sulfate.

Figure 2:
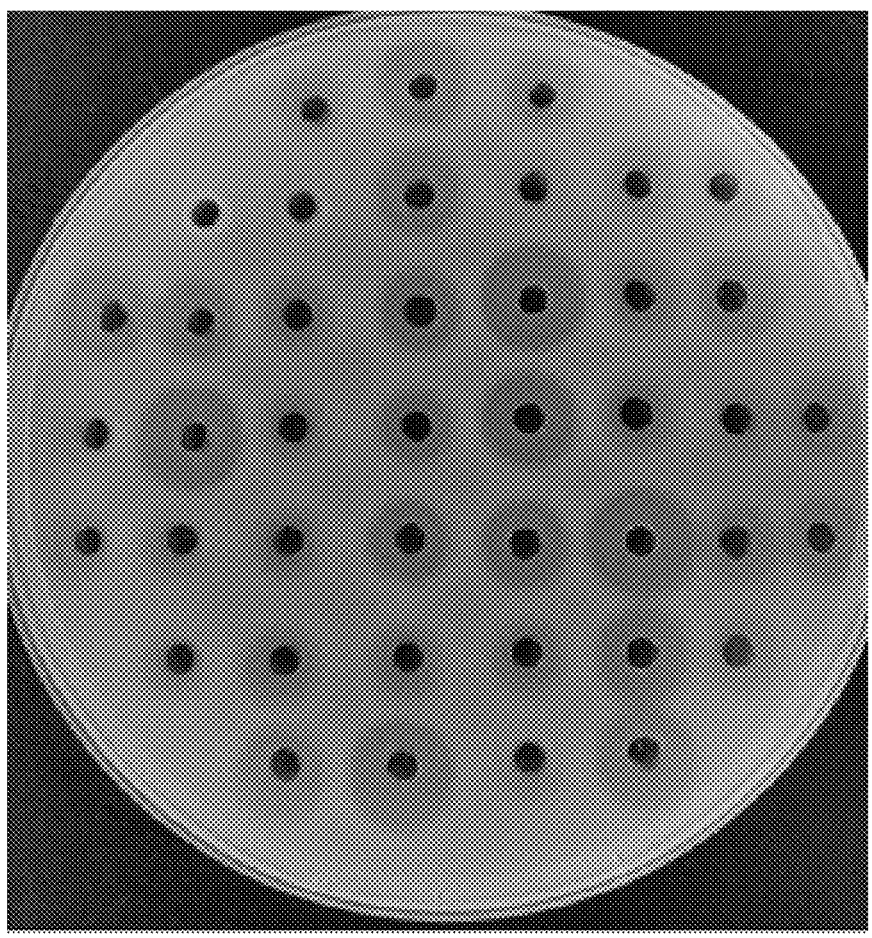
FIG. 2. High throughput screening of the different expression levels of HAase activity using a standard plate.

The quantitation of hyaluronidase activity of culture supernatants was performed with high throughput screening by transparent ring colorimetric plate assay. 2 mg/ml HA was dissolved in citric acid buffer (pH 5.5) to make a HA buffer and 1.5% agarose was melted by heat in the same citric buffer. Equal volume of HA buffer and heated agarose buffer was mixed and poured into a plastic plate to allow solidification. Multiple holes were drilled in the agarose plate as shown in FIG. 2. After centrifuged at 4000 rpm for 5 min, 150 μL supernatant of the fermentation broth of RBS mutant strains was added to the holes in the agarose plate and cultivated at 37° C. for 10 hours. After that, 2.5 g/L cetyltrimethyl ammonium bromide was added and incubated for 30 min. Results (FIG. 2) demonstrated that the mutant strains with RBS modifications exhibit significantly different levels of HAse expression. E168THR1/pP43-DU-PBMS and E168THR2/pP43-DU-PBMS were two mutant strains with different RBS translational strengths.

Example 5

Fed-batch Fermentation of the Recombinant Strains in a 3-L Fermentor

Recombinant strains E168T/pP43-DU-PBMS, E168TH/pP43-DU-PBMS, E168THR1/pP43-DU-PBMS and E168THR2/pP43-DU-PBMS4 were fermented, respectively.

The recombinant strains were grown in a LB medium with 50 μg/ml kanamycin at 37° C. and 200 rpm for 12 hours. The 3-L fermentor contained an initial 1.35 L of fermentation medium (2% Yeast extract, 1.5% sucrose, 15.6 g/L sodium dihydrogen phosphate and 3.9 g/L potassium sulfate, pH 7.0). The seed cultures were transferred into the fermentor with a 10% inoculation volume. Xylose with a final concentration of 20 g/L was used to induce the expression of hasA at 2 hours after the inoculation.

Feed started at about 8 hours after inoculation with a simple sucrose solution at index-fed-batch feed rates of 7.5, 7.5, 15.0, 10.0 g·h$^{-1}$·L$^{-1}$ for the first 4 hours. The constant feed rate was maintained at 5 g·h$^{-1}$·L$^{-1}$ until the end of fermentation. Samples were periodically withdrawn to determine the HA production and HAase activity of the fermentation. After centrifugation at 10000 rpm for 10 min, the fermentation supernatant was transferred to another tube, and 2 volumes ethanol was added to precipitate HA and incubated for 1 hour. The precipitate was collected by centrifugation (10000 rpm for 20 min) and redissolved in equal volume 1 mol·L$^{-1}$ NaCl solution. The suspension was used for further determination of yield and molecular weight.

Figure 3:
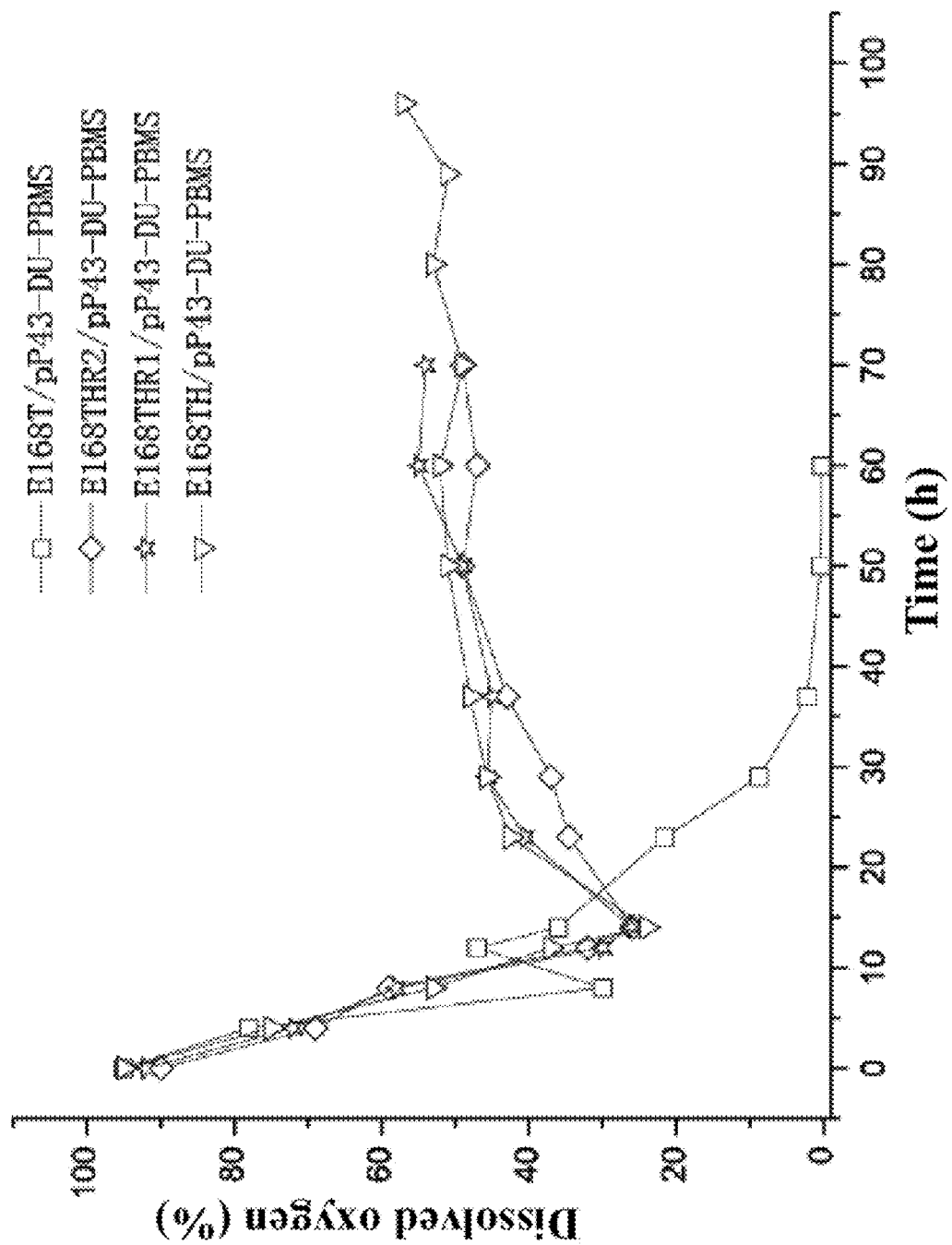
FIG. 3. The curve of dissolved oxygen (DO) in recombinant strains with different expression levels of HAase cultured in a 3 L fermentor.
Figure 4:
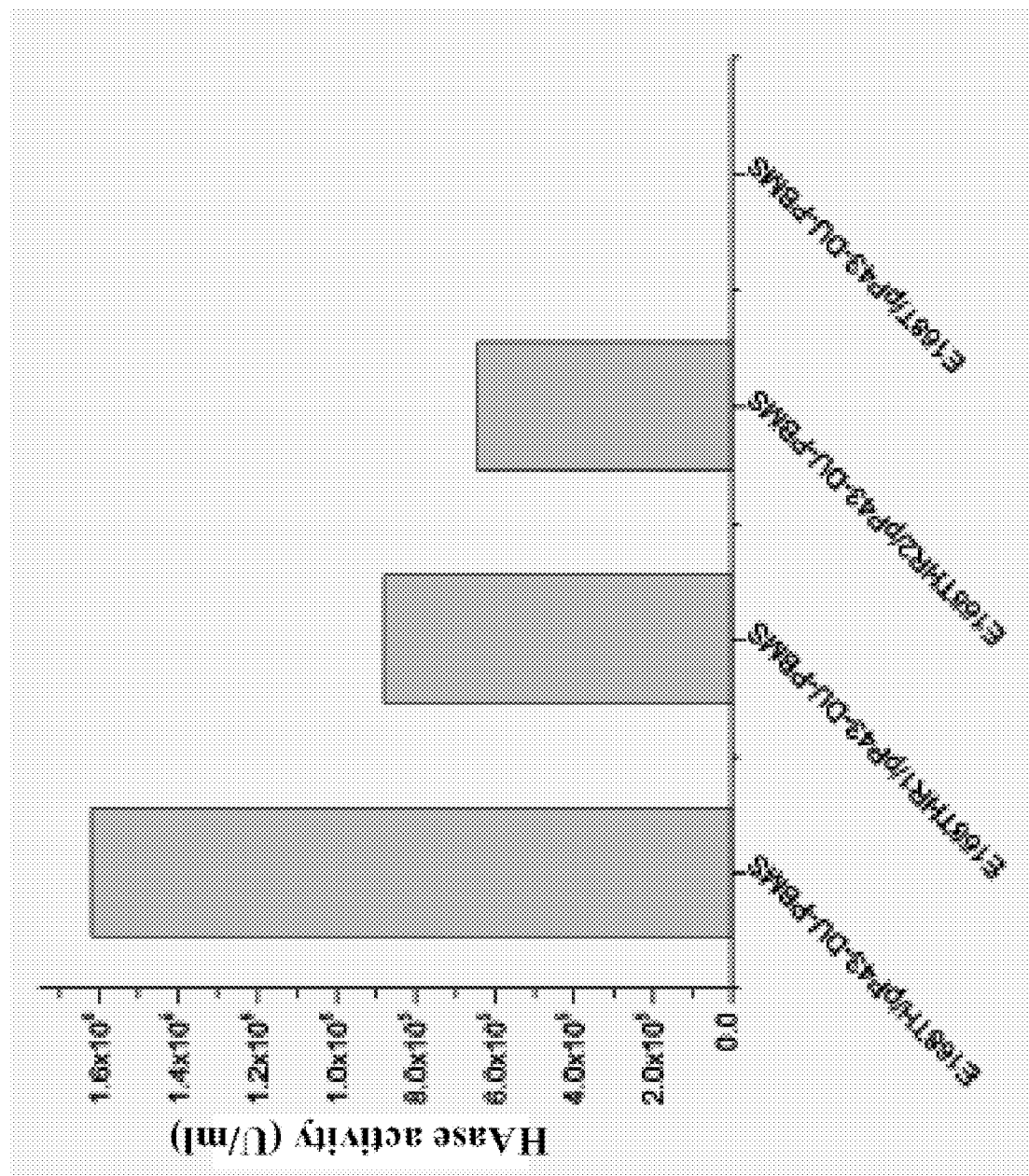
FIG. 4. The HAase activity of recombinant strains with different expression levels of HAase cultured in a 3 L fermentor.
Figure 5:
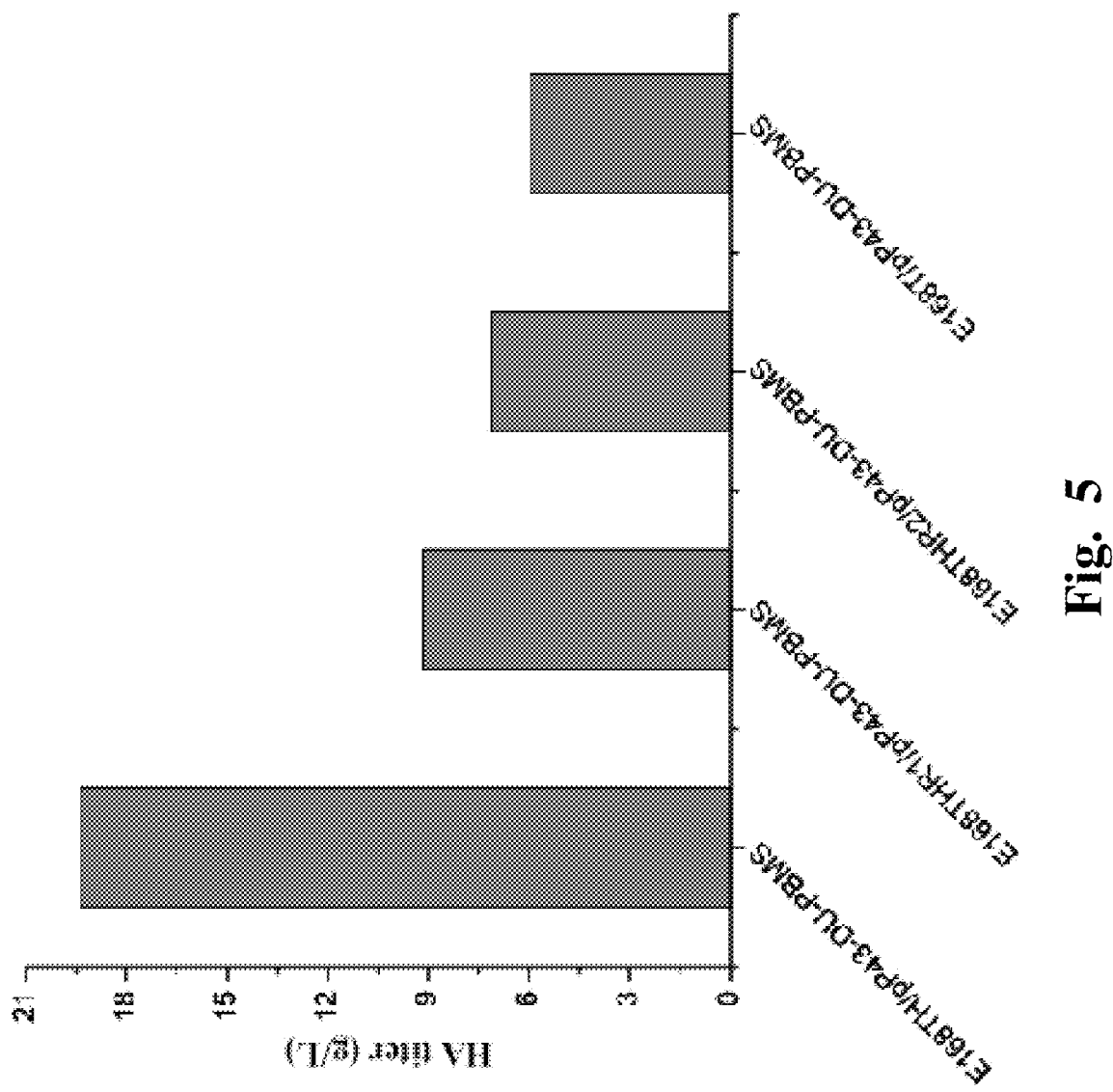
FIG. 5. The production of HA of recombinant strains with different expression levels of HAase cultured in a 3 L fermentor.

Due to the viscoelastic properties of HA, the fermentation of engineered strain E168T/pP43-DU-PBMS became very viscous after 15 h and concomitantly resulting in the dramatic decline of dissolved oxygen (DO), which seriously affected the growth of cells and the accumulation of HA. FIG. 3 showed that the fermentation DO of E168T/pP43-DU-PBMS was almost reduced to 0 at 40 hours, while the fermentation DO of other engineered strains which had different expression levels of HAase were maintained at a higher level. The HAase activities of E168TH/pP43-DU-PBMS, E168THR1/pP43-DU-PBMS and E168THR2/pP43-DU-PBMS4 reached high values of 1.62×10$^6$U/mL, 8.8×10$^5$U/mL and 6.4×10$^4$ U/mL, respectively. The HA yield of E168T/pP43-DU-PBMS reached the maximal HA titer of 5.96 g·L$^{-1}$ due to viscous fermentation. However, the HA yield of the highest HAase expression strain, E168TH/pP43-DU-PBMS, reached 19.38 g·L$^{-1}$, and the HA yield of the other two strains, E168THR1/pP43-DU-PBMS and E168THR2/pP43-DU-PBMS4, with lower HAase expression reached 9.18 g·L$^{-1}$ and 7.13 g·L$^{-1}$, respectively. These results demonstrated that the higher is the HAase production, the higher is the HA yield.

Figure 6:
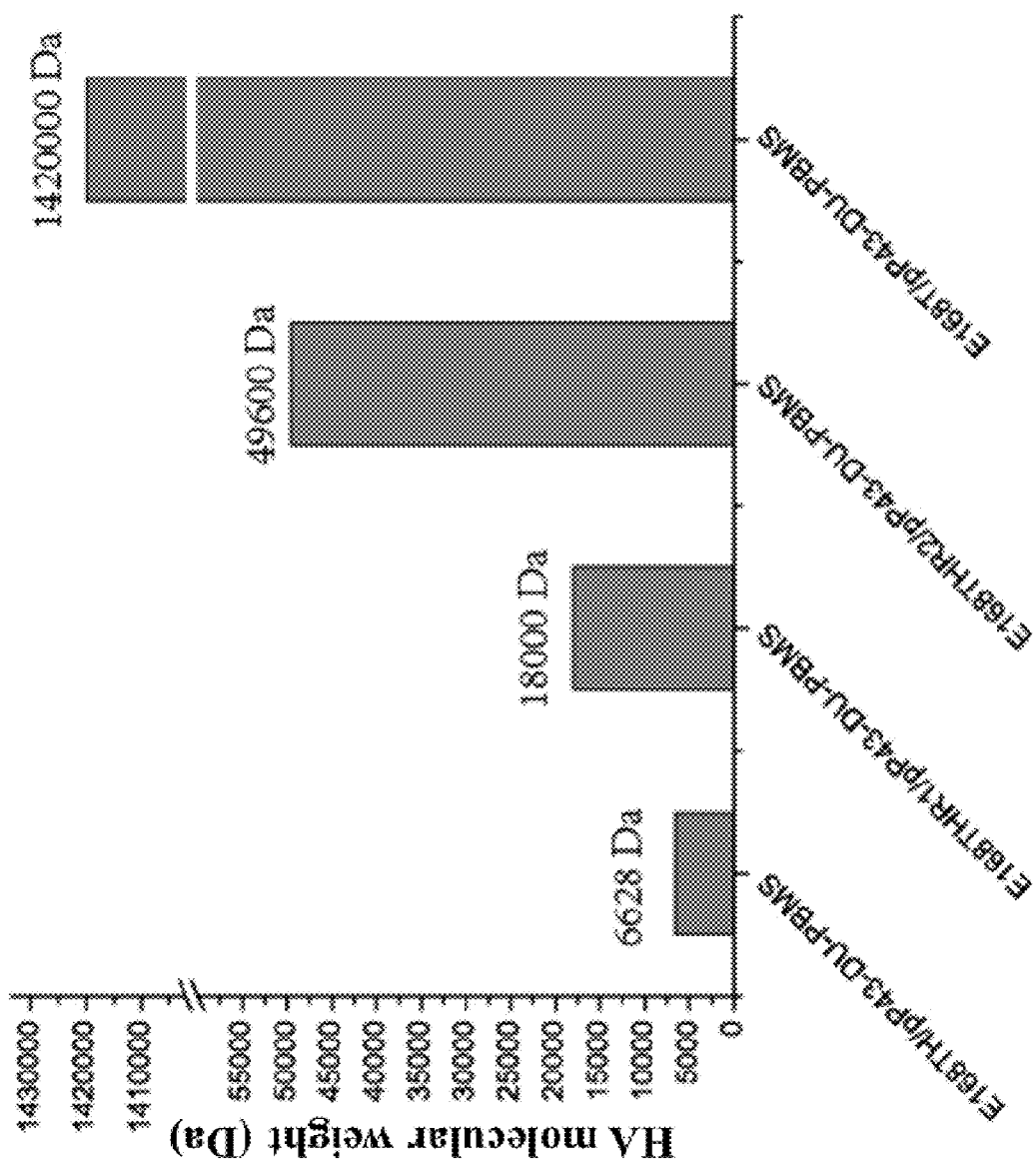
FIG. 6. The average molecular weight of HA produced in different recombinant strains.

There was a significant difference between the average molecular weight of HA of engineered strains with different HAase expression levels (shown in FIG. 6). The average molecular weight of HA from strain E168T/pP43-DU-PBMS which did not express the HAase was 1.42×10$^6$ Da, while those of strains E168TH/pP43-DU-PBMS, E168THR1/pP43-DU-PBMS and E168THR2/pP43-DU-PBMS4 were 6628 Da, 18000 Da and 49600 Da, respectively.

The results showed that the molecular weight of HA could be precisely controlled within a range from 10$^3$ to 10$^6$ Da through controlling the expression level of HAase. Additionally, HA10, HA8, HA6, HA4 and other oligosaccharides could be obtained by allowing the supernatant of the fermentation broth to incubate at room temperature for additional 1-3 hours.

* * *

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

Sequence Listing

```
<210> 1
<211> 1254
<212> DNA
<213> Streptococcus zooepidemicus
<400> 1
atgagaacat taaaaaacct cataactgtt gtggccttta gtattttttg ggtactgttg      60
atttacgtca atgtttatct ctttggtgct aaaggaagct tgtcaattta tggcttttg      120 ctgatagctt acctattagt caaaatgtcc ttatcctttt tttacaagcc atttaaggga    180
agggctgggc aatataaggt tgcagccatt attccctctt ataacgaaga tgctgagtca    240
ttgctagaga ccttaaaaag tgttcagcag caaacctatc ccctagcaga aatttatgtt    300
gttgacgatg aagtgctga tgagacaggt attaagcgca ttgaagacta tgtgcgtgac     360
actggtgacc tatcaagcaa tgtcattgtt caccggtcag aaaaaaatca aggaaagcgt    420
catgcacagg cctgggcctt tgaaagatca gacgctgatg tcttttttgac cgttgactca   480 gatacttata tctaccctga tgctttagag gagttgttaa aaacctttaa tgacccaact    540 gttttttgctg cgacgggtca ccttaatgtc agaaatagac aaaccaatct cttaacacgc   600
ttgacagata ttcgctatga taatgctttt ggcgttgaac gagctgccca atccgttaca    660
ggtaatattc tcgtttgctc aggcccgctt agcgtttaca gacgcgaggt ggttgttcct    720
aacatagata gatacatcaa ccagaccttc ctgggtattc ctgtaagtat cggtgatgac    780
aggtgcttga ccaactatgc aactgattta ggaaagactg tttatcaatc cactgctaaa    840
tgtattacag atgttcctga caagatgtct acttacttga agcagcaaaa ccgctggaac    900
aagtccttct ttagagagtc cattatttct gttaagaaaa tcatgaacaa tccttttgta    960
gccctatgga ccatacttga ggtgtctatg tttatgatgc ttgtttattc tgtggtggat   1020
ttctttgtag gcaatgtcag agaatttgat tggctcaggg ttttggcctt tctggtgatt   1080
atcttcattg ttgctctttg tcgtaatatt cactatatgc ttaagcaccc gctgtccttc   1140
ttgttatctc cgttttatgg ggtactgcat ttgtttgtcc tacagccctt gaaattgtat   1200 tctctttta ctattagaaa tgctgactgg ggaacacgta aaaaattatt ataa          1254

<211> 1386
<212> DNA
<213> Bacillus subtilis
<400> 2
atgaaaaaaa tagctgtcat tggaacaggt tatgtaggac tcgtatcagg cacttgcttt     60
gcggagatcg gcaataaagt tgtttgctgt gatatcgatg aatcaaaaat cagaagcctg    120
aaaaatgggg taatcccaat ctatgaacca gggcttgcag acttagttga aaaaaatgtg    180
ctggatcagc gcctgacctt tacgaacgat atcccgtctg ccattcgggc ctcagatatt    240
atttatattg cagtcggaac gcctatgtcc aaaacaggtg aagctgattt aacgtacgtc    300
aaagcggcgg cgaaaacaat cggtgagcat cttaacggct acaaagtgat cgtaaataaa    360
agcacagtcc cggttggaac agggaaactg gtgcaatcta tcgttcaaaa agcctcaaag    420
gggagatact catttgatgt tgtatctaac cctgaattcc ttcgggaagg gtcagcgatt    480
catgacacga tgaatatgga gcgtgccgtg attggttcaa caagtcataa agccgctgcc    540
atcattgagg aacttcatca gccattccat gctcctgtca ttaaaacaaa cctagaaagt    600
gcagaaatga ttaaatacgc cgcgaatgca tttctggcga caaagatttc ctttatcaac    660
gatatcgcaa acatttgtga gcgagtcggc gcagacgttt caaagttgc tgatggtgtt    720 ggtcttgaca gccgtatcgg cagaaagttc cttaaagctg gtattggatt cggcggttca    780
tgttttccaa aggatacaac cgcgctgctt caaatcgcaa aatcggcagg ctatccattc    840
```

| | |
|---|---|
| aagctcatcg aagctgtcat tgaaacgaac gaaaagcagc gtgttcatat tgtagataaa | 900 |
| cttttgactg ttatgggaag cgtcaaaggg agaaccattt cagtcctggg attagccttc | 960 |
| aaaccgaata cgaacgatgt gagatccgct ccagcgcttg atattatccc aatgctgcag | 1020 |
| cagctgggcg cccatgtaaa agcatacgat ccgattgcta ttcctgaagc ttcagcgatc | 1080 |
| cttggcgaac aggtcgagta ttacacagat gtgtatgctg cgatggaaga cactgatgca | 1140 |
| tgcctgattt taacggattg gccggaagtg aaagaaatgg agcttgtaaa agtgaaaacc | 1200 |
| ctcttaaaac agccagtcat cattgacggc agaaatttat tttcacttga agagatgcag | 1260 |
| gcagccggat acatttatca ctctatcggc cgtcccgctg ttcggggaac ggaaccctct | 1320 |
| gacaagtatt ttccgggctt gccgcttgaa gaattggcta agacttggg aagcgtcaat | 1380 |
| ttataa | 1386 |

<210> 3
<211> 1371
<212> DNA
<213> Bacillus subtilis
<400> 3

| | |
|---|---|
| atggataagc ggtttgcagt tgttttagcg gctggacaag gaacgagaat gaaatcgaag | 60 |
| ctttataaag tccttcatcc agtttgcggt aagcctatgg tagagcacgt cgtggacgaa | 120 |
| gccttaaaat tatctttatc aaagcttgtc acgattgtcg gacatggtgc ggaagaagtg | 180 |
| aaaaagcagc ttggtgataa aagcgagtac gcgcttcaag caaaacagct tggcactgct | 240 |
| catgctgtaa aacaggcaca gccatttctt gctgacgaaa aaggcgtcac aattgtcatt | 300 |
| tgcggagata cgccgctttt gacagcagag acgatggaac agatgctgaa agaacataca | 360 |
| caaagagaag cgaaagctac gattttaact gcggttgcag aagatccaac tggatacggc | 420 |
| cgcattattc gcagcgaaaa cggagcggtt caaaaaatag ttgagcataa ggacgcctct | 480 |
| gaagaagaac gtcttgtaac tgagatcaac accggtacgt attgttttga caatgaagcg | 540 |
| ctatttcggg ctattgatca ggtgtctaat gataatgcac aaggcgagta ttatttgccg | 600 |
| gatgtcatag agattcttaa aaatgaaggc gaaactgttg ccgcttacca gactggtaat | 660 |
| ttccaagaaa cgctcggagt taatgataga gttgctcttt tcaggcaga acaatttatg | 720 |
| aaagagcgca ttaataaacg gcatatgcaa aatggcgtga cgttgattga cccgatgaat | 780 |
| acgtatattt ctcctgacgc tgttatcgga agcgatactg tgatttaccc tggaactgtg | 840 |
| attaaaggtg aggtgcaaat cggagaagat acgattattg ccctcatac ggagattatg | 900 |
| aatagtgcca ttggcagccg tacggttatt aaacaatcgg tagtcaatca cagtaaagtg | 960 |
| gggaatgatg taaacatagg acctttgct cacatcagac ctgattctgt catcgggaat | 1020 |
| gaagtgaaga tcgggaattt tgtagaaatt aaaaagactc aattcggaga ccgaagcaag | 1080 |
| gcatctcatc taagctatgt cggcgatgct gaggtaggca ctgatgtaaa cctgggctgc | 1140 |
| ggttcaatta ctgtcaatta tgatggaaag aataagtatt tgacaaaaat tgaagatggc | 1200 |
| gcgtttatcg gctgcaattc caacttggtt gcccctgtca cagtcggaga aggcgcttat | 1260 |
| gtggcggcag gttcaactgt tacggaagat gtacctggaa aagcacttgc tattgccaga | 1320 |
| gcgagacaag taaataaaga cgattatgtg aaaaatattc ataaaaaata a | 1371 |

<210> 4
<211> 879
<212> DNA
<213> Bacillus subtilis
<400> 4

| | |
|---|---|
| atgaaaaaag tacgtaaagc cataattcca gcagcaggct taggaacacg ttttcttccg | 60 |

-continued

Sequence Listing

```
gctacgaaag caatgccgaa agaaatgctt cctatcgttg ataaacctac cattcaatac      120
ataattgaag aagctgttga agccggtatt gaagatatta ttatcgtaac aggaaaaagc      180
aagcgtgcga ttgaggatca ttttgattac tctcctgagc ttgaaagaaa cctagaagaa      240
aaaggaaaaa ctgagctgct tgaaaaagtg aaaaaggctt ctaacctggc tgacattcac      300
tatatccgcc aaaaagaacc taaggtctc ggacatgctg tctggtgcgc acgcaacttt       360
atcggcgatg agccgtttgc ggtactgctt ggtgacgata ttgttcaggc tgaaactcca      420
gggttgcgcc aattaatgga tgaatatgaa aaaacacttt cttctattat cggtgttcag      480
caggtgcccg aagaagaaac acaccgctac ggcattattg acccgctgac aagtgaaggc      540
cgccgttatc aggtgaaaaa cttcgttgaa aaaccgccta aaggcacagc accttctaat      600
cttgccatct taggccgtta cgtattcacg cctgagatct tcatgtattt agaagagcag      660
caggttggcg ccggcggaga aattcagctc acagacgcca ttcaaaagct gaatgaaatt      720
caaagagtgt ttgcttacga ttttgaaggc aagcgttatg atgttggtga aaagctcggc      780
tttatcacaa caactcttga atttgcgatg caggataaag agcttcgcga tcagctcgtt      840
ccatttatgg aaggtttact aaacaaagaa gaaatctaa                              879
```

<210> 5
<211> 1347
<212> DNA
<213> *Bacillus subtilis*
<400> 5

```
atgggcaagt attttggaac agacggtgta agaggtgtcg ccaatagtga gcttacacct       60
gagctggcct ttaaagtcgg acgtttcggc ggttatgtgc tgacaaaaga caaacaacgt      120
ccaaaagtgc tgataggccg cgatacacgc atctccggcc atatgctgga gggagcccct      180
gtcgccggac ttttatccat tggcgcagaa gtcatgcgcc tgggtgtcat ttctacacca      240
ggtgtatctt atttgacaaa agcgatggat gcagaggcgg cgtcatgat ttccgcttct       300 cataacccag tgcaggataa cggcatcaaa ttctttgggg agatggatt taagcttct       360 gatgaacagg aggctgaaat tgagcgcctg atggacgaac tgaggataa gctgccaaga      420 cctgtcggag cagaccttgg acttgtaaac gattattttg aaggcggaca aaaatatctg      480
caattcttaa acagacagc tgatgaagat ttcacaggca ttcatgtggc attggactgt      540
gccaatggcg caacgtcatc cttggcgaca cacctgtttg ctgatttaga tgcagatgtt      600
tctacaatgg ggacttcccc gaacggatta acattaatg acggcgtcgg ttcgactcat      660
cccgaagcgc tcagcgcgtt tgtcaaagag aaaaacgcgg atctcggtct tgcgttcgac      720
ggtgacggcg accgcctgat tgctgtcgat gaaaaaggaa atattgtaga cggcgaccaa      780
atcatgtaca tatgctcaaa acatctgaaa tcagagggcc gtttaaagga tgatacagtg      840
gtttcaaccg tgatgagcaa cctcggcttc tataaggcgc tcgaaaaaga aggcatcaaa      900
agcgtgcaga cagctgtcgg cgaccgctac gtagtagaag caatgaaaaa agacggctac      960
aacgtcggcg gagagcagtc aggacatctt attttccttg attacaacac gacaggggac     1020
ggattattgt ctgctattat gctgatgaac actttaaaag caacaggcaa gccgctgtca     1080
gagcttgcag ctgaaatgca agagttcccg cagctgttag tcaatgtgag agtgactgat     1140
aaatataaag ttgaagaaaa tgaaaaagta aagcagtta tttctgaagt tgaaaaagaa       1200
atgaacggcg acgccggat tttggtgcgc ccttcaggaa ctgaaccgct cgtccgtgtc     1260
atggctgaag cgaagacgaa agagctgtgc gatgagtatg tcaatcgcat tgttgaagtc     1320
```

Sequence Listing

```
gtccggtcag aaatgggatt agagtaa                                       1347

<210> 6
<211> 1803
<212> DNA
<213> Bacillus subtilis
<400> 6
atgtgtggaa tcgtaggtta tatcggtcag cttgatgcga aggaaatttt attaaaaggg     60
ttagagaagc ttgagtatcg cggttatgac tctgctggta ttgctgttgc caacgaacag    120
ggaatccatg tgttcaaaga aaaggacgc attgcagatc ttcgtgaagt tgtggatgcc    180
aatgtagaag cgaaagccgg aattgggcat actcgctggg cgacacacgg cgaaccaagc    240
tatctgaacg ctcacccgca tcaaagcgca ctgggccgct ttacacttgt tcacaacggc    300
gtgatcgaga actatgttca gctgaagcaa gagtatttgc aagatgtaga gctcaaaagt    360
gacaccgata cagaagtagt cgttcaagta atcgagcaat tcgtcaatgg aggacttgag    420
acagaagaag cgttccgcaa aacacttaca ctgttaaaag gctcttatgc aattgcttta    480
ttcgataacg acaacagaga acgattttt gtagcgaaaa acaaaagccc tctattagta    540
ggtcttggag atacattcaa cgtcgtagca tctgatgcga tggcgatgct tcaagtaacc    600
aacgaatacg tagagctgat ggataaagaa atggttatcg tcactgatga ccaagttgtc    660
atcaaaaacc ttgatggtga cgtgattaca cgtgcgtctt atattgctga gcttgatgcc    720
agtgatatcg aaaaaggcac gtaccctcac tacatgttga agaaacgga tgagcagcct    780 gttgttatgc gcaaaatcat ccaaacgtat caagatgaaa acggcaagct gtctgtgcct    840
ggcgatatcg ctgccgctgt agcggaagcg gaccgcatct atatcattgg ctgcggaaca    900
agctaccatg caggacttgt cggtaaacaa tatattgaaa tgtgggcaaa cgtgccggtt    960
gaagtgcatg tagcgagtga attctcctac aacatgccgc ttctgtctaa gaaaccgctc   1020
ttcattttcc tttctcaaag cggagaaaca gcagacagcc gcgcggtact cgttcaagtc   1080
aaagcgctcg gacacaaagc cctgacaatc acaaacgtac ctggatcaac gctttctcgt   1140
gaagctgact atacattgct gcttcatgca ggccctgaga tcgctgttgc gtcaacgaaa   1200
gcatacactg cacaaatcgc agttctggcg gttcttgctt ctgtggctgc tgacaaaaat   1260
ggcatcaata tcggatttga cctcgtcaaa gaactcggta tcgctgcaaa cgcaatggaa   1320
gctctatgcg accagaaaga cgaaatggaa atgatcgctc gtgaatacct gactgtatcc   1380
agaaatgctt tcttcatcgg acgcggcctt gactacttcg tatgtgtcga aggcgcactg   1440
aagctgaaag agatttctta catccaggca gaaggttttg ccggcggtga gctaaagcac   1500
ggaacgattg ccttgatcga acaaggaaca ccagtattcg cactggcaac tcaagagcat   1560
gtaaacctaa gcatccgcgg aaacgtcaaa gaagttgctg ctcgcggagc aaacacatgc   1620
atcatctcac tgaaaggcct agacgatgcg gatgacagat tcgtattgcc ggaagtaaac   1680
ccagcgcttg ctccgttggt atctgttgtt ccattgcagc tgatcgctta ctatgctgca   1740
ctgcatcgcg gctgtgatgt ggataaacct cgtaaccttg cgaagagtgt tactgtggag   1800
taa                                                                 1803

<210> 7
<211> 1470
<212> DNA
<213> Leech
<400> 7
atgaaagaga tcgcggtgac aattgacgat aagaacgtta ttgcctctgt cagcgagtca     60
```

| | |
|---|---:|
| ttccatggtg ttgcctttga tgcgtcgtta ttttcaccga aggggttgtg gagctttgtt | 120 |
| gacattacct caccgaaatt gtttaaactc ttggagggtc tctctcctgg ttacttcagg | 180 |
| gttggaggaa cgtttgctaa ctggctgttc tttgacttag atgaaaataa taagtggaaa | 240 |
| gactattggg cttttaaaga taaaacaccc gagactgcaa caatcacaag gaggtggctg | 300 |
| tttcgaaaac aaaacaacct gaaaaaagag acttttgacg acttagtcaa actaaccaaa | 360 |
| ggaagcaaaa tgagactgtt atttgattta aacgctgaag tgagaactgg ttatgaaatt | 420 |
| ggaaagaaaa tgacatccac ttgggatagc tcggaagctg aaaaattatt caaatactgt | 480 |
| gtgtcaaaag gttatggaga taatattgat tgggaacttg gtaatgaacc ggaccatacc | 540 |
| tccgcacaca atcttactga aaagcaagtt ggagaggact ttaaagccct gcataaagtg | 600 |
| ctagagaaat atccgacgtt gaataaagga tcgcttgttg gacctgacgt tggatggatg | 660 |
| ggagtctctt atgtgaaagg attagcagac ggggctggtg atcacgtaac cgctttact | 720 |
| cttcatcagt attattttga cggcaatacc tcagatgtgt caacatacct tgacgctact | 780 |
| tattttaaaa aacttcaaca gctgtttgac aaagttaagg atgtcttgaa aaattctcca | 840 |
| cataaagata aaccgctctg gcttggagaa acaagttctg gatacaacag cggcacaaaa | 900 |
| gatgtatccg atcgatatgt tagcggattt ctaacattgg acaagttggg actcagtgca | 960 |
| gcgaacaatg tgaaagttgt gataagacaa acgatctata atggatacta cggacttctt | 1020 |
| gataaaaata ctctagagcc aaatccggat tattggctaa tgcatgttca caattctctg | 1080 |
| gttggaaata cggtttttaa agttgacgtt agtgaccta caaataaagc tagagtttat | 1140 |
| gcacagtgca ccaaaacaaa tagcaaacat actcagagta gatactacaa gggctcattg | 1200 |
| acgatctttg ctcttaatgt tggagatgaa gatgtgacgt tgaagattga tcaatacagt | 1260 |
| ggaaaaaaga tttattcata tattctgacc ccagaaggcg gccaacttac atcacaaaaa | 1320 |
| gttctttttga atggaaaaga attaaaatta gtgtcggatc aattgccaga actgaatgca | 1380 |
| gacgagtcga aaacctcttt cactctgtct ccaaagacat ttggattttt tgttgttagc | 1440 |
| gatgctaacg ttgaagcctg caaaaaataa | 1470 |

<210> 8
<211> 403
<212> DNA
<213> Artificial sequence
<400> 8

| | |
|---|---:|
| gcctcaatcc taggagaaac agtcacggca aaagatttag tagaaaaaca aaaagagctg | 60 |
| gaaaaggtgg agacattcaa tatgttttca aaagccggaa aagcgctttc ggacaccgta | 120 |
| accaatactg cccagtcaat gtatgaatgg atacgggata tgaatcaata agtacgtgaa | 180 |
| agagaaaagc aacccagata tgatagggaa ctttctctct tcttgtttta cattgaatct | 240 |
| ttacaatcct attgatataa tctaagctag tgtattttgc gtttaatagt aggaggaaag | 300 |
| tggtaccatg ctaaaaagaa cttcattcgt atcttcatta ttcatcagtt cagctgtttt | 360 |
| actatcaatc ttacttcctt cgggccaagc tcatgcagaa ttc | 403 |

<210> 9
<211> 556
<212> DNA
<213> Artificial sequence
<400> 9

| | |
|---|---:|
| gagctcggta cccgggatc ctctagagat tctaccgttc gtatagcata cattatacga | 60 |
| agttatcttg atatggcttt ttatatgtgt tactctacat acagaaagga ggaactaaat | 120 |
| atggccaagt tgaccagtgc cgttccggtg ctcaccgcgc gcgacgtcgc cggagcggtc | 180 |

```
gagttctgga ccgaccggct cgggttctcc cggacttcg tggaggacga cttcgccggt      240
gtggtccggg acgacgtgac cctgttcatc agcgcggtcc aggaccaggt ggtgccggac      300
aacaccctgg cctgggtgtg ggtgcgcggc ctggacgagc tgtacgccga gtggtcggag      360
gtcgtgtcca cgaacttccg ggacgcctcc gggccggcca tgaccgagat cggcgagcag      420
ccgtgggggc gggagttcgc cctgcgcgac ccggccggca ctgcgtgca cttcgtggcc      480 gaggagcagg actgaataac ttcgtatagc atacattata cgaacggtag aatcgtcgac      540
ctgcaggcat gcaagc                                                     556

<210> 10
<211> 268
<212> DNA
<213> Bacillus subtilis
<400> 10
tgataggtgg tatgttttcg cttgaacttt taaatacagc cattgaacat acggttgatt      60
taataactga caaacatcac cctcttgcta aagcggccaa ggacgctgcc gccggggctg     120
tttgcgtttt tgccgtgatt tcgtgtatca ttggtttact tattttttg ccaaagctgt      180 aatggctgaa aattcttaca tttatttac attttagaa atgggcgtga aaaaagcgc        240 gcgattatgt aaaatataaa gtgatagc                                        268

<210> 11
<211> 257
<212> DNA
<213> Bacillus subtilis
<400> 11
ggagttctga gaattggtat gccttataag tccaattaac agttgaaaac ctgcatagga      60
gagctatgcg ggttttttat tttacataat gatacataat ttaccgaaac ttgcggaaca     120
taattgagga atcatagaat tttgtcaaaa taatttatt gacaacgtct tattaacgtt      180
gatataattt aaattttatt tgacaaaaat gggctcgtgt tgtacaataa atgtagttaa      240
aaaggagcga tttacat                                                    257

<210> 12
<211> 403
<212> DNA
<213> Artificial sequence
<400> 12
gcctcaatcc taggagaaac agtcacggca aagatttag tagaaaaaca aaaagagctg       60
gaaaaggtgg agacattcaa tatgttttca aaagccggaa aagcgctttc ggacaccgta     120
accaatactg cccagtcaat gtatgaatgg atacgggata tgaatcaata agtacgtgaa     180
agagaaaagc aacccagata tgatagggaa cttttctctt tcttgtttta cattgaatct     240
ttacaatcct attgatataa tctaagctag tgtattttgc gtttaatagt aagaggagag      300
tggtaccatg ctaaaaagaa cttcattcgt atcttcatta ttcatcagtt cagctgtttt      360
actatcaatc ttacttcctt cgggccaagc tcatgcagaa ttc                       403

<210> 13
<211> 403
<212> DNA
<213> Artificial sequence
<400> 13
gcctcaatcc taggagaaac agtcacggca aagatttag tagaaaaaca aaaagagctg       60
gaaaaggtgg agacattcaa tatgttttca aaagccggaa aagcgctttc ggacaccgta     120
accaatactg cccagtcaat gtatgaatgg atacgggata tgaatcaata agtacgtgaa     180
agagaaaagc aacccagata tgatagggaa cttttctctt tcttgtttta cattgaatct     240
```

| Sequence Listing |
|---|

```
ttacaatcct attgatataa tctaagctag tgtattttgc gtttaatagt acgtagacag    300
tggtaccatg ctaaaaagaa cttcattcgt atcttcatta ttcatcagtt cagctgtttt    360
actatcaatc ttacttcctt cgggccaagc tcatgcagaa ttc                      403

<210> 14
<211> 17
<212> DNA
<213> Artificial sequence
<400> 14
aagagaggaa tgtacac                                                    17

<210> 15
<211> 35
<212> DNA
<213> DNA
<400> 15
cgcggatcca tgagaacatt aaaaaacctc ataac                                35

<210> 16
<211> 33
<212> DNA
<213> Artificial sequence
<400> 16
tgcatgcatt tataataatt ttttacgtgt tcc                                  33

<210> 17
<211> 49
<212> DNA
<213> Artificial sequence
<400> 17
cggggtacca agagaggaat gtacacatga aaaaaatagc tgtcattgg                 49

<210> 18
<211> 31
<212> DNA
<213> Artificial sequence
<400> 18
ccggagctct tataaattga cgcttcccaa g                                    31

<210> 19
<211> 48
<212> DNA
<213> Artificial sequence
<400> 19
cgggagctca agagaggaat gtacacatgg ataagcggtt tgcagttg                  48

<210> 20
<211> 49
<212> DNA
<213> Artificial sequence
<400> 20
ccgctcgagc ggactctagt ctagattatt ttttatgaat atttttcac                 49

<210> 21
<211> 30
<212> DNA
<213> Artificial sequence
<400> 21
ggactagtgg agttctgaga attggtatgc                                      30

<210> 22
<211> 25
<212> DNA
<213> Artificial sequence
<400> 22
atgtaaatcg ctccttttta actac                                           25

<210> 23
<211> 45
<212> DNA
<213> Artificial sequence
<400> 23
gtagttaaaa aggagcgatt tacatatgaa aaagtacgt aaagc                      45

<210> 24
```

```
<211> 51
<212> DNA
<213> Artificial sequence
<400> 24
ggactagtaa gagaggaatg tacacatggg caagtattt ggaacagacg g        51

<210> 25
<211> 52
<212> DNA
<213> Artificial sequence
<400> 25
ccgctcgagc ggactctagt ctagattact ctaatcccat ttctgaccgg ac       52

<210> 26
<211> 51
<212> DNA
<213> Artificial sequence
<400> 26
ggactagtaa gagaggaatg tacacatgtg tggaatcgta ggttatatcg g        51

<210> 27
<211> 49
<212> DNA
<213> Artificial sequence
<400> 27
ccgctcgagc ggactctagt ctagattact ccacagtaac actcttcgc           49

<210> 28
<211> 41
<212> DNA
<213> Artificial sequence
<400> 28
atgcacagtc tgcagaattc caccaccacc accaccacat g                   41

<210> 29
<211> 23
<212> DNA
<213> Artificial sequence
<400> 29
ttactttttg cacgcttcaa cat                                       23

<210> 30
<211> 42
<212> DNA
<213> Artificial sequence
<400> 30
cgcagccaaa ggagtggatt gcctcaatcc taggagaaac ag                  42

<210> 31
<211> 24
<212> DNA
<213> Artificial sequence
<400> 31
gaattctgca gactgtgcat gagc                                      24

<210> 32
<211> 23
<212> DNA
<213> Artificial sequence
<400> 32
tcagctggtc tagatcacta gtc                                       23

<210> 33
<211> 23
<212> DNA
<213> Artificial sequence
<400> 33
aatccactcc tttggctgcg ctc                                       23

<210> 34
<211> 41
<212> DNA
<213> Artificial sequence
<400> 34
ttgaagcgtg caaaaagtaa gagctcggta cccggggatc c                   41

<210> 35
```

```
<211> 22
<212> DNA
<213> Artificial sequence
<400> 35
gcttgcatgc ctgcaggtcg ac                                      22

<210> 36
<211> 45
<212> DNA
<213> Artificial sequence
<400> 36
cgacctgcag gcatgcaagc cacttctttc agacggaacc cttgc             45

<210> 37
<211> 24
<212> DNA
<213> Artificial sequence
<400> 37
cggtcgttca tatagaagtg atag                                    24

<210> 38
<211> 44
<212> DNA
<213> Artificial sequence
<400> 38
cacttctata tgaacgaccg cctgtgtgaa attgttatcc gctc              44

<210> 39
<211> 45
<212> DNA
<213> Artificial sequence
<400> 39
tagtgatcta gaccagctga gtgactggga aaaccctggc gttac             45

<210> 40
<211> 50
<212> DNA
<213> Artificial sequence
<221> misc_feature
<222> (14)..(14)
<223> n is a, c, g, t or u <221> misc_feature
<222> (16)..(16)
<223> n is a, c, g, t or u <221> misc_feature
<222> (18)..(18)
<223> n is a, c, g, t or u <400> 40
acggggtacc actntnynhb yactattaaa cgcaaaatac actagcttag        50

<210> 41
<211> 32
<212> DNA
<213> Artificial sequence
<400> 41
acggggtacc atgctaaaaa gaacttcatt cg                           32
```

---

SEQUENCE LISTING

<160> NUMBER OF SEQ ID NOS: 41

<210> SEQ ID NO 1
<211> LENGTH: 1254
<212> TYPE: DNA
<213> ORGANISM: Streptococcus zooepidemicus

<400> SEQUENCE: 1
atgagaacat taaaaaacct cataactgtt gtggccttta gtattttttg ggtactgttg    60
atttacgtca atgtttatct ctttggtgct aaaggaagct tgtcaattta tggctttttg   120

```
ctgatagctt acctattagt caaaatgtcc ttatcctttt tttacaagcc atttaaggga      180
agggctgggc aatataaggt tgcagccatt attccctctt ataacgaaga tgctgagtca      240
ttgctagaga ccttaaaaag tgttcagcag caaacctatc ccctagcaga aatttatgtt      300
gttgacgatg gaagtgctga tgagacaggt attaagcgca ttgaagacta tgtgcgtgac      360
actggtgacc tatcaagcaa tgtcattgtt caccggtcag aaaaaaatca aggaaagcgt      420
catgcacagg cctgggcctt tgaaagatca gacgctgatg tcttttttgac cgttgactca      480 gatacttata tctaccctga tgctttagag gagttgttaa aaacctttaa tgacccaact      540 gttttttgctg cgacgggtca ccttaatgtc agaaatagac aaaccaatct cttaacacgc      600
ttgacagata ttcgctatga taatgctttt ggcgttgaac gagctgccca atccgttaca      660
ggtaatattc tcgtttgctc aggcccgctt agcgtttaca gacgcgaggt ggttgttcct      720
aacatagata gatacatcaa ccagaccttc ctgggtattc ctgtaagtat cggtgatgac      780
aggtgcttga ccaactatgc aactgattta ggaaagactg tttatcaatc cactgctaaa      840
tgtattacag atgttcctga caagatgtct acttacttga agcagcaaaa ccgctggaac      900
aagtccttct ttagagagtc cattatttct gttaagaaaa tcatgaacaa tccttttgta      960
gccctatgga ccatacttga ggtgtctatg tttatgatgc ttgtttattc tgtggtggat     1020
ttctttgtag gcaatgtcag agaatttgat tggctcaggg ttttggcctt tctggtgatt     1080
atcttcattg ttgctctttg tcgtaatatt cactatatgc ttaagcaccc gctgtccttc     1140
ttgttatctc cgttttatgg ggtactgcat ttgtttgtcc tacagccctt gaaattgtat     1200 tctctttta ctattagaaa tgctgactgg ggaacacgta aaaaattatt ataa            1254

<210> SEQ ID NO 2
<211> LENGTH: 1386
<212> TYPE: DNA
<213> ORGANISM: Bacillus subtilis

<400> SEQUENCE: 2
atgaaaaaaa tagctgtcat tggaacaggt tatgtaggac tcgtatcagg cacttgcttt       60
gcggagatcg gcaataaagt tgtttgctgt gatatcgatg aatcaaaaat cagaagcctg      120
aaaaatgggg taatcccaat ctatgaacca gggcttgcag acttagttga aaaaaatgtg      180
ctggatcagc gcctgacctt tacgaacgat atcccgtctg ccattcgggc ctcagatatt      240
atttatattg cagtcggaac gcctatgtcc aaaacaggtg aagctgattt aacgtacgtc      300
aaagcggcgg cgaaaacaat cggtgagcat cttaacggct acaaagtgat cgtaaataaa      360
agcacagtcc cggttggaac agggaaactg gtgcaatcta tcgttcaaaa agcctcaaag      420
gggagatact catttgatgt tgtatctaac cctgaattcc ttcgggaagg tcagcgattt      480
catgacacga tgaatatgga gcgtgccgtg attggttcaa caagtcataa agccgctgcc      540
atcattgagg aacttcatca gccattccat gctcctgtca ttaaaacaaa cctagaaagt      600
gcagaaatga ttaaatacgc cgcgaatgca tttctggcga caaagatttc ctttatcaac      660
gatatcgcaa acatttgtga gcgagtcggc gcagacgttt caaagttgc tgatggtgtt      720 ggtcttgaca gccgtatcgg cagaaagttc cttaaagctg gtattggatt cggcggttca      780
tgttttccaa aggatacaac cgcgctgctt caaatcgcaa aatcggcagg ctatccattc      840
aagctcatcg aagctgtcat tgaaacgaac gaaaagcagc gtgttcatat tgtagataaa      900
cttttgactg ttatgggaag cgtcaaaggg agaaccattt cagtcctggg attagccttc      960
```

```
aaaccgaata cgaacgatgt gagatccgct ccagcgcttg atattatccc aatgctgcag    1020
cagctgggcg cccatgtaaa agcatacgat ccgattgcta ttcctgaagc ttcagcgatc    1080
cttggcgaac aggtcgagta ttacacagat gtgtatgctg cgatggaaga cactgatgca    1140
tgcctgattt taacggattg gccggaagtg aaagaaatgg agcttgtaaa agtgaaaacc    1200
ctcttaaaac agccagtcat cattgacggc agaaatttat tttcacttga agagatgcag    1260
gcagccggat acatttatca ctctatcggc cgtcccgctg ttcggggaac ggaaccctct    1320
gacaagtatt ttccgggctt gccgcttgaa gaattggcta aagacttggg aagcgtcaat    1380
ttataa                                                               1386

<210> SEQ ID NO 3
<211> LENGTH: 1371
<212> TYPE: DNA
<213> ORGANISM: Bacillus subtilis

<400> SEQUENCE: 3
atggataagc ggtttgcagt tgttttagcg gctggacaag gaacgagaat gaaatcgaag      60
ctttataaag tccttcatcc agtttgcggt aagcctatgg tagagcacgt cgtggacgaa     120
gccttaaaat tatctttatc aaagcttgtc acgattgtcg acatggtgc ggaagaagtg      180 aaaaagcagc ttggtgataa agcgagtac gcgcttcaag caaacagct tggcactgct       240 catgctgtaa acaggcaca gccatttctt gctgacgaaa aaggcgtcac aattgtcatt      300
tgcggagata cgccgctttt gacagcagag acgatggaac agatgctgaa agaacataca     360
caaagagaag cgaaagctac gattttaact gcggttgcag aagatccaac tggatacggc     420
cgcattattc gcagcgaaaa cggagcggtt caaaaaatag ttgagcataa ggacgcctct     480
gaagaagaac gtcttgtaac tgagatcaac accggtacgt attgttttga caatgaagcg    540
ctatttcggg ctattgatca ggtgtctaat gataatgcac aaggcgagta ttatttgccg    600
gatgtcatag agattcttaa aaatgaaggc gaaactgttg ccgcttacca gactggtaat    660
ttccaagaaa cgctcggagt taatgataga gttgctcttt ctcaggcaga acaatttatg    720
aaagagcgca ttaataaacg gcatatgcaa atggcgtga cgttgattga cccgatgaat     780
acgtatattt ctcctgacgc tgttatcgga agcgatactg tgatttaccc tggaactgtg    840
attaaaggtg aggtgcaaat cggagaagat acgattattg cccctcatac ggagattatg    900
aatagtgcca ttggcagccg tacggttatt aaacaatcgg tagtcaatca cagtaaagtg    960
gggaatgatg taaacatagg acctttttgct cacatcagac ctgattctgt catcgggaat   1020
gaagtgaaga tcgggaattt tgtagaaatt aaaaagactc aattcggaga ccgaagcaag   1080
gcatctcatc taagctatgt cggcgatgct gaggtaggca ctgatgtaaa cctgggctgc   1140
ggttcaatta ctgtcaatta tgatggaaag aataagtatt tgacaaaaat tgaagatggc   1200
gcgtttatcg gctgcaattc caacttggtt gcccctgtca cagtcggaga aggcgcttat   1260
gtggcggcag gttcaactgt tacgaagat gtacctggaa aagcacttgc tattgccaga    1320
gcgagacaag taaataaaga cgattatgtg aaaaatattc ataaaaaata a           1371

<210> SEQ ID NO 4
<211> LENGTH: 879
<212> TYPE: DNA
<213> ORGANISM: Bacillus subtilis

<400> SEQUENCE: 4
atgaaaaaag tacgtaaagc cataattcca gcagcaggct taggaacacg ttttcttccg     60
```

```
gctacgaaag caatgccgaa agaaatgctt cctatcgttg ataaacctac cattcaatac    120
ataattgaag aagctgttga agccggtatt gaagatatta ttatcgtaac aggaaaaagc    180
aagcgtgcga ttgaggatca ttttgattac tctcctgagc ttgaaagaaa cctagaagaa    240
aaaggaaaaa ctgagctgct tgaaaaagtg aaaaaggctt ctaacctggc tgacattcac    300
tatatccgcc aaaaagaacc taaaggtctc ggacatgctg tctggtgcgc acgcaacttt    360
atcggcgatg agccgtttgc ggtactgctt ggtgacgata ttgttcaggc tgaaactcca    420
gggttgcgcc aattaatgga tgaatatgaa aaaacacttt cttctattat cggtgttcag    480
caggtgcccg aagaagaaac acaccgctac ggcattattg acccgctgac aagtgaaggc    540
cgccgttatc aggtgaaaaa cttcgttgaa aaaccgccta aaggcacagc accttctaat    600
cttgccatct taggccgtta cgtattcacg cctgagatct tcatgtattt agaagagcag    660
caggttggcg ccggcggaga aattcagctc acagacgcca ttcaaaagct gaatgaaatt    720
caaagagtgt ttgcttacga ttttgaaggc aagcgttatg atgttggtga aaagctcggc    780
tttatcacaa caactcttga atttgcgatg caggataaag agcttcgcga tcagctcgtt    840
ccatttatgg aaggtttact aaacaaagaa gaaatctaa                          879

<210> SEQ ID NO 5
<211> LENGTH: 1347
<212> TYPE: DNA
<213> ORGANISM: Bacillus subtilis

<400> SEQUENCE: 5
atgggcaagt attttggaac agacggtgta agaggtgtcg ccaatagtga gcttacacct     60
gagctggcct ttaaagtcgg acgtttcggc ggttatgtgc tgacaaaaga caaacaacgt    120
ccaaaagtgc tgataggccg cgatacacgc atctccggcc atatgctgga gggagcccTt    180
gtcgccggac ttttatccat tggcgcagaa gtcatgcgcc tgggtgtcat ttctacacca    240
ggtgtatctt atttgacaaa agcgatggat gcagaggcgg gcgtcatgat ttccgcttct    300
cataacccag tgcaggataa cggcatcaaa ttctttgggg gagatggatt taagcttTct    360
gatgaacagg aggctgaaat tgagcgcctg atggacgaac tgaggataaa gctgccaaga    420
cctgtcggag cagaccttgg acttgtaaac gattattttg aaggcggaca aaaatatctg    480
caattcttaa acagacagc tgatgaagat ttcacaggca ttcatgtggc attggactgt    540
gccaatggcg caacgtcatc cttggcgaca cacctgtttg ctgatttaga tgcagatgtt    600 tctcaatgg ggacttcccc gaacggatta acattaatg acggcgtcgg ttcgactcat    660
cccgaagcgc tcagcgcgtt tgtcaaagag aaaaacgcgg atctcggtct tgcgttcgac    720
ggtgacggcg accgctgat tgctgtcgat gaaaaaggaa atattgtaga cggcgaccaa    780
atcatgtaca tatgctcaaa acatctgaaa tcagagggcc gtttaaagga tgatacagtg    840
gtttcaaccg tgatgagcaa cctcggcttc tataagcgc tcgaaaaaga aggcatcaaa    900
agcgtgcaga cagctgtcgg cgaccgctac gtagtagaag caatgaaaaa agacggctac    960
aacgtcggcg gagagcagtc aggacatctt atttTccttg attacaacac gacaggggac   1020
ggattattgt ctgctattat gctgatgaac actttaaaag caacaggcaa gccgctgtca   1080
gagcttgcag ctgaaatgca gaagttcccg cagctgttag tcaatgtgag agtgactgat   1140
aaatataaag ttgaagaaaa tgaaaaagta aaagcagtta tttctgaagt tgaaaaagaa   1200
atgaacggcg acggccggat tttggtgcgc ccttcaggaa ctgaaccgct cgtccgtgtc   1260
```

| atggctgaag cgaagacgaa agagctgtgc gatgagtatg tcaatcgcat tgttgaagtc | 1320 |
| gtccggtcag aaatgggatt agagtaa | 1347 |

<210> SEQ ID NO 6
<211> LENGTH: 1803
<212> TYPE: DNA
<213> ORGANISM: Bacillus subtilis

<400> SEQUENCE: 6

| atgtgtggaa tcgtaggtta tatcggtcag cttgatgcga aggaaatttt attaaaaggg | 60 |
| ttagagaagc ttgagtatcg cggttatgac tctgctggta ttgctgttgc caacgaacag | 120 |
| ggaatccatg tgttcaaaga aaaggacgc attgcagatc ttcgtgaagt tgtggatgcc | 180 |
| aatgtagaag cgaaagccgg aattgggcat actcgctggg cgacacacgg cgaaccaagc | 240 |
| tatctgaacg ctcacccgca tcaaagcgca ctgggccgct ttacacttgt tcacaacggc | 300 |
| gtgatcgaga actatgttca gctgaagcaa gagtatttgc aagatgtaga gctcaaaagt | 360 |
| gacaccgata cagaagtagt cgttcaagta atcgagcaat cgtcaatgg aggacttgag | 420 |
| acagaagaag cgttccgcaa aacacttaca ctgttaaaag gctcttatgc aattgcttta | 480 |
| ttcgataacg acaacagaga acgatttttt gtagcgaaaa acaaaagccc tctattagta | 540 |
| ggtcttggag atacattcaa cgtcgtagca tctgatgcga tggcgatgct tcaagtaacc | 600 |
| aacgaatacg tagagctgat ggataaagaa atggttatcg tcactgatga ccaagttgtc | 660 |
| atcaaaaacc ttgatggtga cgtgattaca cgtgcgtctt atattgctga gcttgatgcc | 720 |
| agtgatatcg aaaaaggcac gtaccctcac tacatgttga agaaacgga tgagcagcct | 780 |
| gttgttatgc gcaaaatcat ccaaacgtat caagatgaaa acggcaagct gtctgtgcct | 840 |
| ggcgatatcg ctgccgctgt agcggaagcg gaccgcatct atatcattgg ctgcggaaca | 900 |
| agctaccatg caggacttgt cggtaaacaa tatattgaaa tgtgggcaaa cgtgccggtt | 960 |
| gaagtgcatg tagcgagtga attctcctac aacatgccgc ttctgtctaa gaaaccgctc | 1020 |
| ttcattttcc tttctcaaag cggagaaaca gcagacagcc gcgcggtact cgttcaagtc | 1080 |
| aaagcgctcg gacacaaagc cctgacaatc acaaacgtac ctggatcaac gctttctcgt | 1140 |
| gaagctgact atacattgct gcttcatgca ggccctgaga tcgctgttgc gtcaacgaaa | 1200 |
| gcatacactg cacaaatcgc agttctggcg gttcttgctt ctgtggctgc tgacaaaaat | 1260 |
| ggcatcaata tcggatttga cctcgtcaaa gaactcggta tcgctgcaaa cgcaatggaa | 1320 |
| gctctatgcg accagaaaga cgaaatgaaa atgatcgctc gtaataccct gactgtatcc | 1380 |
| agaaatgctt tcttcatcgg acgcggcctt gactacttcg tatgtgtcga aggcgcactg | 1440 |
| aagctgaaag agatttctta catccaggca gaaggttttg ccggcggtga gctaaagcac | 1500 |
| ggaacgattg ccttgatcga acaaggaaca ccagtattcg cactggcaac tcaagagcat | 1560 |
| gtaaacctaa gcatccgcgg aaacgtcaaa gaagttgctg ctcgcggagc aaacacatgc | 1620 |
| atcatctcac tgaaaggcct agacgatgcg gatgacagat tcgtattgcc ggaagtaaac | 1680 |
| ccagcgcttg ctccgttggt atctgttgtt ccattgcagc tgatcgctta ctatgctgca | 1740 |
| ctgcatcgcg gctgtgatgt ggataaacct cgtaaccttg cgaagagtgt tactgtggag | 1800 |
| taa | 1803 |

<210> SEQ ID NO 7
<211> LENGTH: 1470
<212> TYPE: DNA
<213> ORGANISM: Hirudo nipponia

<400> SEQUENCE: 7

```
atgaaagaga tcgcggtgac aattgacgat aagaacgtta ttgcctctgt cagcgagtca    60
ttccatggtg ttgcctttga tgcgtcgtta ttttcaccga aggggttgtg gagctttgtt   120
gacattacct caccgaaatt gtttaaactc ttggagggtc tctctcctgg ttacttcagg   180
gttggaggaa cgtttgctaa ctggctgttc tttgacttag atgaaaataa taagtggaaa   240
gactattggg cttttaaaga taaaacaccc gagactgcaa caatcacaag gaggtggctg   300
tttcgaaaac aaaacaacct gaaaaagag acttttgacg acttagtcaa actaaccaaa   360
ggaagcaaaa tgagactgtt atttgattta acgctgaag tgagaactgg ttatgaaatt    420
ggaaagaaaa tgacatccac ttgggatagc tcggaagctg aaaaattatt caaatactgt   480
gtgtcaaaag gttatggaga taatattgat tgggaacttg gtaatgaacc ggaccatacc   540
tccgcacaca atcttactga aaagcaagtt ggagaggact ttaaagccct gcataaagtg   600
ctagagaaat atccgacgtt gaataaagga tcgcttgttg acctgacgt tggatggatg    660
ggagtctctt atgtgaaagg attagcagac ggggctggtg atcacgtaac cgcttttact   720
cttcatcagt attattttga cggcaatacc tcagatgtgt caacatacct tgacgctact   780
tattttaaaa aacttcaaca gctgtttgac aaagttaagg atgtcttgaa aaattctcca   840
cataaagata aaccgctctg gcttggagaa acaagttctg gatacaacag cggcacaaaa   900
gatgtatccg atcgatatgt tagcggattt ctaacattgg acaagttggg actcagtgca   960
gcgaacaatg tgaaagttgt gataagacaa acgatctata atggatacta cggacttctt  1020
gataaaaata ctctagagcc aaatccggat tattggctaa tgcatgttca caattctctg  1080
gttggaaata cggttttaa agttgacgtt agtgacccta caaataaagc tagagtttat   1140
gcacagtgca ccaaaacaaa tagcaaacat actcagagta gatactacaa gggctcattg  1200
acgatcttg ctcttaatgt tggagatgaa gatgtgacgt tgaagattga tcaatacagt    1260
ggaaaaaaga tttattcata tattctgacc ccagaaggcg gccaacttac atcacaaaaa  1320
gttcttttga tggaaaaga attaaaatta gtgtcggatc aattgccaga actgaatgca   1380
gacgagtcga aaacctcttt cactctgtct ccaaagacat ttggattttt tgttgttagc  1440
gatgctaacg ttgaagcctg caaaaaataa                                   1470
```

<210> SEQ ID NO 8
<211> LENGTH: 403
<212> TYPE: DNA
<213> ORGANISM: Artificial sequence
<220> FEATURE:
<223> OTHER INFORMATION: Synthetic DNA

<400> SEQUENCE: 8

```
gcctcaatcc taggagaaac agtcacggca aaagatttag tagaaaaaca aaaagagctg    60
gaaaaggtgg agacattcaa tatgttttca aaagccggaa aagcgctttc ggacaccgta   120
accaatactg cccagtcaat gtatgaatgg atacgggata tgaatcaata agtacgtgaa   180
agagaaaagc aacccagata tgataggaa cttttctctt tcttgtttta cattgaatct   240
ttacaatcct attgatataa tctaagctag tgtattttgc gtttaatagt aggaggaaag   300
tggtaccatg ctaaaagaa cttcattcgt atcttcatta ttcatcagtt cagctgtttt   360
actatcaatc ttacttcctt cgggccaagc tcatgcagaa ttc                    403
```

<210> SEQ ID NO 9

```
<211> LENGTH: 556
<212> TYPE: DNA
<213> ORGANISM: Artificial sequence
<220> FEATURE:
<223> OTHER INFORMATION: Synthetic DNA

<400> SEQUENCE: 9
gagctcggta cccggggatc tctagagat  tctaccgttc gtatagcata cattatacga      60
agttatcttg atatggcttt ttatatgtgt tactctacat acagaaagga ggaactaaat     120
atggccaagt tgaccagtgc cgttccggtg ctcaccgcgc gcgacgtcgc cggagcggtc     180
gagttctgga ccgaccggct cgggttctcc cgggacttcg tggaggacga cttcgccggt     240
gtggtccggg acgacgtgac cctgttcatc agcgcggtcc aggaccaggt ggtgccggac     300
aacaccctgg cctgggtgtg ggtgcgcggc ctggacgagc tgtacgccga gtggtcggag     360
gtcgtgtcca cgaacttccg ggacgcctcc gggccggcca tgaccgagat cggcgagcag     420
ccgtgggggc gggagttcgc cctgcgcgac ccggccggca actgcgtgca cttcgtggcc     480
gaggagcagg actgaataac ttcgtatagc atacattata cgaacggtag aatcgtcgac     540
ctgcaggcat gcaagc                                                    556

<210> SEQ ID NO 10
<211> LENGTH: 268
<212> TYPE: DNA
<213> ORGANISM: Bacillus subtilis

<400> SEQUENCE: 10
tgataggtgg tatgtttcg cttgaacttt taaatacagc cattgaacat acggttgatt      60
taataactga caaacatcac cctcttgcta aagcggccaa ggacgctgcc gccggggctg     120
tttgcgtttt tgccgtgatt tcgtgtatca ttggtttact tattttttg ccaaagctgt      180 aatggctgaa aattcttaca tttattttac attttttagaa atgggcgtga aaaaaagcgc    240
gcgattatgt aaaatataaa gtgatagc                                       268

<210> SEQ ID NO 11
<211> LENGTH: 257
<212> TYPE: DNA
<213> ORGANISM: Bacillus subtilis

<400> SEQUENCE: 11
ggagttctga gaattggtat gccttataag tccaattaac agttgaaaac ctgcatagga      60
gagctatgcg ggttttttat tttacataat gatacataat ttaccgaaac ttgcggaaca     120
taattgagga atcatagaat tttgtcaaaa taatttatt gacaacgtct tattaacgtt      180
gatataattt aaatttatt tgacaaaaat gggctcgtgt tgtacaataa atgtagttaa      240
aaaggagcga tttacat                                                   257

<210> SEQ ID NO 12
<211> LENGTH: 403
<212> TYPE: DNA
<213> ORGANISM: Artificial sequence
<220> FEATURE:
<223> OTHER INFORMATION: Synthetic DNA

<400> SEQUENCE: 12
gcctcaatcc taggagaaac agtcacggca aagatttag tagaaaaaca aaaagagctg       60
gaaaaggtgg agacattcaa tatgtttca aaagccggaa aagcgctttc ggacaccgta      120
accaatactg cccagtcaat gtatgaatgg atacgggata tgaatcaata agtacgtgaa    180
```

```
agagaaaagc aacccagata tgatagggaa cttttctctt tcttgtttta cattgaatct    240
ttacaatcct attgatataa tctaagctag tgtattttgc gtttaatagt aagaggagag    300
tggtaccatg ctaaaaagaa cttcattcgt atcttcatta ttcatcagtt cagctgtttt    360
actatcaatc ttacttcctt cgggccaagc tcatgcagaa ttc                      403
```

```
<210> SEQ ID NO 13
<211> LENGTH: 403
<212> TYPE: DNA
<213> ORGANISM: Artificial sequence
<220> FEATURE:
<223> OTHER INFORMATION: Synthetic DNA

<400> SEQUENCE: 13
gcctcaatcc taggagaaac agtcacggca aaagatttag tagaaaaaca aaaagagctg     60
gaaaaggtgg agacattcaa tatgttttca aaagccggaa aagcgctttc ggacaccgta    120
accaatactg cccagtcaat gtatgaatgg atacgggata tgaatcaata agtacgtgaa    180
agagaaaagc aacccagata tgatagggaa cttttctctt tcttgtttta cattgaatct    240
ttacaatcct attgatataa tctaagctag tgtattttgc gtttaatagt acgtagacag    300
tggtaccatg ctaaaaagaa cttcattcgt atcttcatta ttcatcagtt cagctgtttt    360
actatcaatc ttacttcctt cgggccaagc tcatgcagaa ttc                      403
```

```
<210> SEQ ID NO 14
<211> LENGTH: 17
<212> TYPE: DNA
<213> ORGANISM: Artificial sequence
<220> FEATURE:
<223> OTHER INFORMATION: Synthetic DNA

<400> SEQUENCE: 14
aagagaggaa tgtacac                                                    17
```

```
<210> SEQ ID NO 15
<211> LENGTH: 35
<212> TYPE: DNA
<213> ORGANISM: Artificial sequence
<220> FEATURE:
<223> OTHER INFORMATION: Primer Sequence

<400> SEQUENCE: 15
cgcggatcca tgagaacatt aaaaaacctc ataac                                35
```

```
<210> SEQ ID NO 16
<211> LENGTH: 33
<212> TYPE: DNA
<213> ORGANISM: Artificial sequence
<220> FEATURE:
<223> OTHER INFORMATION: Primer Sequence

<400> SEQUENCE: 16
tgcatgcatt tataataatt ttttacgtgt tcc                                  33
```

```
<210> SEQ ID NO 17
<211> LENGTH: 49
<212> TYPE: DNA
<213> ORGANISM: Artificial sequence
<220> FEATURE:
<223> OTHER INFORMATION: Primer Sequence

<400> SEQUENCE: 17
```
cggggtacca agagaggaat gtacacatga aaaaaatagc tgtcattgg                49

<210> SEQ ID NO 18
<211> LENGTH: 31
<212> TYPE: DNA
<213> ORGANISM: Artificial sequence
<220> FEATURE:
<223> OTHER INFORMATION: Primer Sequence

<400> SEQUENCE: 18
ccggagctct tataaattga cgcttcccaa g                                  31

<210> SEQ ID NO 19
<211> LENGTH: 48
<212> TYPE: DNA
<213> ORGANISM: Artificial sequence
<220> FEATURE:
<223> OTHER INFORMATION: Primer Sequence

<400> SEQUENCE: 19
cgggagctca agagaggaat gtacacatgg ataagcggtt tgcagttg                48

<210> SEQ ID NO 20
<211> LENGTH: 49
<212> TYPE: DNA
<213> ORGANISM: Artificial sequence
<220> FEATURE:
<223> OTHER INFORMATION: Primer Sequence

<400> SEQUENCE: 20
ccgctcgagc ggactctagt ctagattatt ttttatgaat attttttcac              49

<210> SEQ ID NO 21
<211> LENGTH: 30
<212> TYPE: DNA
<213> ORGANISM: Artificial sequence
<220> FEATURE:
<223> OTHER INFORMATION: Primer Sequence

<400> SEQUENCE: 21
ggactagtgg agttctgaga attggtatgc                                    30

<210> SEQ ID NO 22
<211> LENGTH: 25
<212> TYPE: DNA
<213> ORGANISM: Artificial sequence
<220> FEATURE:
<223> OTHER INFORMATION: Primer Sequence

<400> SEQUENCE: 22
atgtaaatcg ctcctttttta actac                                        25

<210> SEQ ID NO 23
<211> LENGTH: 45
<212> TYPE: DNA
<213> ORGANISM: Artificial sequence
<220> FEATURE:
<223> OTHER INFORMATION: Primer Sequence

<400> SEQUENCE: 23
gtagttaaaa aggagcgatt tacatatgaa aaaagtacgt aaagc                   45

<210> SEQ ID NO 24
<211> LENGTH: 51
<212> TYPE: DNA
<213> ORGANISM: Artificial sequence

```
<220> FEATURE:
<223> OTHER INFORMATION: Primer Sequence

<400> SEQUENCE: 24
ggactagtaa gagaggaatg tacacatggg caagtatttt ggaacagacg g         51

<210> SEQ ID NO 25
<211> LENGTH: 52
<212> TYPE: DNA
<213> ORGANISM: Artificial sequence
<220> FEATURE:
<223> OTHER INFORMATION: Primer Sequence

<400> SEQUENCE: 25
ccgctcgagc ggactctagt ctagattact ctaatcccat ttctgaccgg ac        52

<210> SEQ ID NO 26
<211> LENGTH: 51
<212> TYPE: DNA
<213> ORGANISM: Artificial sequence
<220> FEATURE:
<223> OTHER INFORMATION: Primer Sequence

<400> SEQUENCE: 26
ggactagtaa gagaggaatg tacacatgtg tggaatcgta ggttatatcg g         51

<210> SEQ ID NO 27
<211> LENGTH: 49
<212> TYPE: DNA
<213> ORGANISM: Artificial sequence
<220> FEATURE:
<223> OTHER INFORMATION: Primer Sequence

<400> SEQUENCE: 27
ccgctcgagc ggactctagt ctagattact ccacagtaac actcttcgc           49

<210> SEQ ID NO 28
<211> LENGTH: 41
<212> TYPE: DNA
<213> ORGANISM: Artificial sequence
<220> FEATURE:
<223> OTHER INFORMATION: Primer Sequence

<400> SEQUENCE: 28
atgcacagtc tgcagaattc caccaccacc accaccacat g                   41

<210> SEQ ID NO 29
<211> LENGTH: 23
<212> TYPE: DNA
<213> ORGANISM: Artificial sequence
<220> FEATURE:
<223> OTHER INFORMATION: Primer Sequence

<400> SEQUENCE: 29
ttactttttg cacgcttcaa cat                                       23

<210> SEQ ID NO 30
<211> LENGTH: 42
<212> TYPE: DNA
<213> ORGANISM: Artificial sequence
<220> FEATURE:
<223> OTHER INFORMATION: Primer Sequence

<400> SEQUENCE: 30
cgcagccaaa ggagtggatt gcctcaatcc taggagaaac ag                  42
```

<210> SEQ ID NO 31
<211> LENGTH: 24
<212> TYPE: DNA
<213> ORGANISM: Artificial sequence
<220> FEATURE:
<223> OTHER INFORMATION: Primer Sequence

<400> SEQUENCE: 31
gaattctgca gactgtgcat gagc					24

<210> SEQ ID NO 32
<211> LENGTH: 23
<212> TYPE: DNA
<213> ORGANISM: Artificial sequence
<220> FEATURE:
<223> OTHER INFORMATION: Primer Sequence

<400> SEQUENCE: 32
tcagctggtc tagatcacta gtc					23

<210> SEQ ID NO 33
<211> LENGTH: 23
<212> TYPE: DNA
<213> ORGANISM: Artificial sequence
<220> FEATURE:
<223> OTHER INFORMATION: Primer Sequence

<400> SEQUENCE: 33
aatccactcc tttggctgcg ctc					23

<210> SEQ ID NO 34
<211> LENGTH: 41
<212> TYPE: DNA
<213> ORGANISM: Artificial sequence
<220> FEATURE:
<223> OTHER INFORMATION: Primer Sequence

<400> SEQUENCE: 34
ttgaagcgtg caaaaagtaa gagctcggta cccggggatc c					41

<210> SEQ ID NO 35
<211> LENGTH: 22
<212> TYPE: DNA
<213> ORGANISM: Artificial sequence
<220> FEATURE:
<223> OTHER INFORMATION: Primer Sequence

<400> SEQUENCE: 35
gcttgcatgc ctgcaggtcg ac					22

<210> SEQ ID NO 36
<211> LENGTH: 45
<212> TYPE: DNA
<213> ORGANISM: Artificial sequence
<220> FEATURE:
<223> OTHER INFORMATION: Primer Sequence

<400> SEQUENCE: 36
cgacctgcag gcatgcaagc cacttctttc agacggaacc cttgc					45

<210> SEQ ID NO 37
<211> LENGTH: 24
<212> TYPE: DNA
<213> ORGANISM: Artificial sequence
<220> FEATURE:
<223> OTHER INFORMATION: Primer Sequence

```
<400> SEQUENCE: 37
cggtcgttca tatagaagtg atag                                          24

<210> SEQ ID NO 38
<211> LENGTH: 44
<212> TYPE: DNA
<213> ORGANISM: Artificial sequence
<220> FEATURE:
<223> OTHER INFORMATION: Primer Sequence

<400> SEQUENCE: 38
cacttctata tgaacgaccg cctgtgtgaa attgttatcc gctc                    44

<210> SEQ ID NO 39
<211> LENGTH: 45
<212> TYPE: DNA
<213> ORGANISM: Artificial sequence
<220> FEATURE:
<223> OTHER INFORMATION: Primer Sequence

<400> SEQUENCE: 39
tagtgatcta gaccagctga gtgactggga aaaccctggc gttac                   45

<210> SEQ ID NO 40
<211> LENGTH: 50
<212> TYPE: DNA
<213> ORGANISM: Artificial sequence
<220> FEATURE:
<223> OTHER INFORMATION: Primer Sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 40
acggggtacc actntnynhb yactattaaa cgcaaaatac actagcttag              50

<210> SEQ ID NO 41
<211> LENGTH: 32
<212> TYPE: DNA
<213> ORGANISM: Artificial sequence
<220> FEATURE:
<223> OTHER INFORMATION: Primer Sequence

<400> SEQUENCE: 41
acggggtacc atgctaaaaa gaacttcatt cg                                 32
```

What is claimed is:

1. A recombinant *Bacillus subtilis* bacterium having a hyaluronic acid (HA) biosynthetic pathway, which is further transformed to express and secrete hyaluronidase.

2. The *Bacillus subtilis* bacterium of claim 1, wherein the bacterium is transformed with a DNA fragment having a constitutive promoter and a ribosome binding site sequence and encoding a signal peptide and hyaluronidase.

3. The *Bacillus subtilis* bacterium of claim 2, wherein the expression of hyaluronidase is regulated by ribosomal binding sites having different translational strengths.

4. The *Bacillus subtilis* bacterium of claim 2, wherein the DNA fragment comprises the nucleic acid sequence of SEQ ID NO: 8, SEQ ID NO: 12, or SEQ ID NO: 13.

5. The *Bacillus subtilis* bacterium of claim 1, wherein said HA biosynthetic pathway comprises a heterologous hyaluronan synthase hasA gene derived from *Streptococcus zooepidemicus, Streptococcus equi*, or *Streptococcus equissp*.

6. The *Bacillus subtilus* bacterium of claim 1, wherein said HA biosynthetic pathway comprises a UDP-glucose dehydrogenase gene tauD, UDP-N-acetylglucosamine pyrophosphorylase gene glmU, UDP-glucose pyrophosphorylase gene gtaB, mutase gene glmM, and amino transferase gene glmS, said genes derived from *Steptococcus* species, *Escherichia coli*, and/or *Bacillus* species.

7. A method for making a *Bacillus subtilis* bacterium cell culture capable of providing specific molecular weight hyaluronic acid, said method comprising the steps of:
 1) transforming said bacterium with a hasA gene which encodes a hyaluronan synthase, said gene is integrated into the chromosome of said bacterium by use of plasmid pAX01:
 2) transforming said bacterium with genes tuaD which encodes an UDP-glucose dehydrogenase, glmU which encodes a UDP-N-acetylglucosamine pyrophosphorylase, gtaB which encodes a UDP-glucose pyrophosphorylase, glmM which encodes a mutase, and glmS which encodes an amino transferase, said genes are connected in series and inserted into vector pP43NMK, said vector is transformed into the bacterium;
 3) coexpressing in said bacterium a hyaluronidase gene fused with a regulatory DNA fragment containing a promoter, a ribosome binding site (RBS) sequence and encoding a signal peptide, said DNA fragment is integrated onto the chromosome of the bacterium;

wherein said bacterium expresses hyaluronic acid that is acted on by the hyaluronidase to provide specific molecular weight hyaluronic acid in said cell culture.

8. The method of claim 7 further comprising regulating expression levels of hyaluronidase by using ribosomal binding site mutants with different translational strengths to control the expression levels of hyaluronidase.

9. The method of claim 7, wherein said *Bacillus subtilis* bacterium cell culture is fermented at 30-37° C. and pH 6.0-7.0 for 48-96 hours with glucose or sucrose as the carbon source for fermentation.

10. A method of producing specific-molecular-weight HA or HA oligosaccharides using a recombinant *Bacillus subtilis* bacterium of claim 1, comprising the steps of:
 a) culturing said recombinant *Bacillus subtilis* bacterium at 30-37° C. and pH 6.0-7.0 for 48-96 hours with glucose or sucrose as the carbon source; and
 b) purifying specific-molecular-weight HA or HA oligosaccharides from the culture of said recombinant *Bacillus subtilis* bacterium.

* * * * *